US009791383B2

(12) United States Patent
Gaukroger

(10) Patent No.: US 9,791,383 B2
(45) Date of Patent: Oct. 17, 2017

(54) INSPECTION SYSTEM FOR AND METHOD OF INSPECTING DEPOSITS PRINTED ON WORKPIECES

(75) Inventor: David Alexander Gaukroger, Dorchester (GB)

(73) Assignee: ASM ASSEMBLY SYSTEMS SWITZERLAND GMBH, Zurich (CH)

( * ) Notice: Subject to any disclaimer, the term of this patent is extended or adjusted under 35 U.S.C. 154(b) by 1327 days.

(21) Appl. No.: 10/561,495

(22) PCT Filed: Jun. 18, 2004

(86) PCT No.: PCT/GB2004/002649
§ 371 (c)(1),
(2), (4) Date: Jun. 16, 2006

(87) PCT Pub. No.: WO2004/114217
PCT Pub. Date: Dec. 29, 2004

(65) Prior Publication Data
US 2006/0222234 A1    Oct. 5, 2006

(30) Foreign Application Priority Data

Jun. 19, 2003 (GB) .................................. 0314233.8

(51) Int. Cl.
*G06K 9/00* (2006.01)
*G01N 21/956* (2006.01)
(Continued)

(52) U.S. Cl.
CPC ..... *G01N 21/95684* (2013.01); *G06T 7/0004* (2013.01); *G06T 7/0008* (2013.01); *H05K 3/1216* (2013.01); *H05K 1/0269* (2013.01)

(58) Field of Classification Search
CPC ....... G06T 7/0008; G06T 7/00; G06T 7/0002; G06T 7/0004; G06T 7/0006; G06T 7/001;
(Continued)

(56) References Cited

U.S. PATENT DOCUMENTS 4,578,810 A * 3/1986 MacFarlane et al. ........ 382/147
5,982,927 A * 11/1999 Koljonen ................ G06T 7/001
382/145

(Continued)

FOREIGN PATENT DOCUMENTS

CN      1262025       8/2000
JP      H07-040526    2/1995
(Continued)

*Primary Examiner* — Eric Rush
(74) *Attorney, Agent, or Firm* — Renner, Otto, Boisselle and Sklar, LLP

(57) ABSTRACT

An inspection system for and method of inspecting deposits printed on workpieces through a printing screen, the system comprising: a camera unit movable relative to a printing screen, where comprising a body including a plurality of apertures, and a workpiece on which deposits are printed through the apertures of the printing screen; and a control unit operable to control the camera unit such as to capture images of at least one pair of corresponding regions of the printing screen and the workpiece, and process the images to determine, for each of a plurality of points defining the image of the printing screen, whether the point is of aperture, and, only where the point is of aperture, determine whether the corresponding point of the corresponding image of the workpiece, as defined by a corresponding plurality of points, is of deposit, thereby enabling a determination of a print characteristic of deposits printed on the workpiece from a relationship of the points determined to be of deposit to the points determined to be of aperture.

45 Claims, 17 Drawing Sheets

(51) Int. Cl.
    *G06T 7/00*     (2017.01)
    *H05K 3/12*     (2006.01)
    *H05K 1/02*     (2006.01)

(58) Field of Classification Search
    CPC . G06T 2207/30108; G06T 2207/30141; G06T 2207/30144; G06T 2207/30148; G06T 2207/30152; H05K 1/0266; H05K 1/0269; H05K 3/1216
    USPC ................ 382/140, 141, 144–150; 703/6
    See application file for complete search history.

(56) References Cited

U.S. PATENT DOCUMENTS

| | | | | |
|---|---|---|---|---|
| 6,317,513 | B2 * | 11/2001 | Michael ............... | G06T 7/001 382/145 |
| 6,347,583 | B1 * | 2/2002 | Isogai et al. ............... | 382/149 |
| 6,522,776 | B1 * | 2/2003 | Ehrichs ............... | 382/144 |
| 6,574,358 | B1 * | 6/2003 | Koljonen et al. ............. | 382/147 |
| 6,606,402 | B2 * | 8/2003 | Wagman ............... | 382/150 |
| 6,621,517 | B1 * | 9/2003 | Squibb ............... | G03F 9/00 348/131 |
| 6,687,402 | B1 * | 2/2004 | Taycher et al. ............... | 382/199 |
| 6,738,505 | B1 * | 5/2004 | Prince ............... | 382/150 |
| 6,810,138 | B1 * | 10/2004 | Schanz ............... | 382/144 |

FOREIGN PATENT DOCUMENTS

| | | |
|---|---|---|
| JP | H08-001907 | 1/1996 |
| JP | H11-186711 | 7/1999 |
| JP | A11340292 | 12/1999 |
| JP | H11-344449 | 12/1999 |
| JP | 2000/187734 | 7/2000 |
| JP | 2002/508067 | 3/2002 |
| WO | 9902021 | 1/1999 |

* cited by examiner

INSPECTION SYSTEM FOR AND METHOD OF INSPECTING DEPOSITS PRINTED ON WORKPIECES

This application is a national phase of International Application No. PCT/GB2004/002649 filed Jun. 18, 2004 and published in the English language.

The present invention relates to an inspection system for and a method of inspecting deposits printed on workpieces, typically substrates, such as circuit boards.

Existing inspection systems, such as utilized in the screen printing machines available from the present applicant, DEK International GmbH (Zurich, Switzerland), and also disclosed in EP-A-1000529, provide both for a simple determination of the overall deposit coverage as a percentage of the expected deposit coverage, and more complex determinations which include the deposit coverage of each deposit as a percentage of the expected deposit coverage, the alignment of the deposits to structures, such as pads, actual or near bridging between adjacent deposits and structures, and also inspection of the printing screen for blocked apertures or smearing.

These existing inspection systems generally utilize the camera unit which is utilized in aligning the printing screen and an introduced workpiece to acquire an image of a region of the workpiece and, where screen inspection is performed, an image of the printing screen at a plurality of inspection sites.

In one determination, the image of the workpiece at each inspection site is processed to identify the regions of structures, typically pads, which are not covered by deposits, and the areas of those regions are compared with the previously-learnt full areas of the structures to determine the areas of the deposits on the structures. The resulting values are then reported as percentages of deposit coverage.

For each inspection site that is to be inspected, a learning step is required to determine the size and location of each of the structures on the workpiece on which deposits are to be printed and the size and location of each of the expected deposits. The percentage of deposit coverage for any printed deposit can then be determined by reference to a perfect deposit, or the corresponding aperture in the printing screen on the basis that the area of the printed deposit should match that of the aperture in the printing screen through which the deposit was printed.

In order to achieve an acceptable throughput of workpieces through a screen printing machine, only a limited period of time can be allocated to inspection. An image of a workpiece, such as a printed circuit board, is complex, in including printed paste, unprinted pads, tracks, bare board, solder resist, tracks covered with solder resist and printed legends, thereby requiring complex image processing to interpret the image. In requiring complex image processing, the time required to complete the image processing is lengthy, restricting the number of inspection sites, and thereby the area of a workpiece, which can be inspected in a given, allocated period of time.

Also, existing inspection systems require the camera unit to be accurately positioned when the workpiece image is captured at each inspection site, as otherwise the image which is captured will not correspond to the image previously-learnt for that inspection site, and thus not contain the set of structures, such as pads on a printed circuit board, which have been learnt, thereby leading to errors in inspection. Thus, the camera unit has to be stopped and referenced at each inspection site, contributing to the inspection time. Even then, the positioning may not be sufficiently accurate as to avoid mis-alignment.

Furthermore, existing inspection systems require the generation and storage of large amounts of data relating to the structures on a workpiece and the apertures in a printing screen at each inspection site. In dealing with such large amounts of data, data processing is particularly time consuming.

It is an aim of the present invention to provide an improved inspection system for inspecting deposits printed on workpieces, typically substrates, such as circuit boards, a screen printing machine incorporating the same, and an improved inspection method of inspecting deposits printed on workpieces, typically substrates, such as circuit boards.

In one aspect the present invention provides an inspection system for inspecting deposits printed on workpieces through a printing screen, the system comprising: a camera unit movable relative to a printing screen, where comprising a body including a plurality of apertures, and a workpiece on which deposits are printed through the apertures of the printing screen; and a control unit operable to control the camera unit such as to capture images of at least one pair of corresponding regions of the printing screen and the workpiece, and process the images to determine, for each of a plurality of points defining the image of the printing screen, whether the point is of aperture, and, only where the point is of aperture, determine whether the corresponding point of the corresponding image of the workpiece, as defined by a corresponding plurality of points, is of deposit, thereby enabling a determination of a print characteristic of deposits printed on the workpiece from a relationship of the points determined to be of deposit to the points determined to be of aperture.

Preferably, the camera unit is operable simultaneously to capture images of the printing screen and the workpiece.

In one embodiment the camera unit is a full-area camera unit for capturing full-area images of the printing screen and the workpiece.

In another embodiment the camera unit is a line-scan camera unit for capturing line-scan images of the printing screen and the workpiece.

In one embodiment the control unit is configured simultaneously to process the images of the printing screen and the workpiece during capture by the camera unit.

In another embodiment the control unit is configured to process the captured images subsequent to acquisition.

In one embodiment the images of the printing screen and the workpiece are defined by respective ones of screen and workpiece signals having intensities in dependence upon imaged features, with the points defining each of the images being time-sliced components of the respective screen and workpiece signals.

Preferably, the relationship of the points determined to be of deposit to the points determined to be of aperture is determined from a time count of a time for which the workpiece signal is determined to be of deposit relative to a time for which the screen signal is determined to be of aperture.

In another embodiment the images of the printing screen and the workpiece are pixelated images, with the points defining each of the images being pixels of the pixelated images.

Preferably, the relationship of the points determined to be of deposit to the points determined to be of aperture is determined from a number count of the number of pixels determined to be of deposit relative to the number of pixels determined to be of aperture.

In one embodiment the control unit is configured to acquire a plurality of pairs of corresponding images of the printing screen and the workpiece in accordance with an inspection schedule defining a plurality of inspection sites at which images are in use acquired.

Preferably, the inspection sites of the inspection schedule are determined in a set-up routine.

More preferably, an offset in the corresponding pair of images of the printing screen and the workpiece as acquired by the camera unit at each inspection site is predetermined, such that the pixel in an image of the workpiece corresponding to a pixel in the corresponding image of the printing screen is determined in accordance with the offset.

In one embodiment the print characteristic comprises a representation of a percentage of a determined deposit coverage as compared to an expected deposit coverage.

In one embodiment the print characteristic is provided as a representation for all deposits.

Preferably, the representation is of a worst case deposit.

In another embodiment the print characteristic is provided as a plurality of representations for the inspection sites.

In one embodiment the representation for each inspection site is of a worst case deposit in the respective inspection site.

In another embodiment the representation for each inspection site comprises a plurality of representations corresponding to at least ones or groups of ones of the deposits in the respective inspection site.

Preferably, the points determined to be of deposit are determined by reference to a reference threshold value of image intensity.

In one embodiment, for at least one of the apertures, the points determined to be of deposit are determined as having an image intensity one of above or below a reference threshold value of image intensity.

In one embodiment, for at least one of the apertures, the points determined to be of deposit are determined as having an image intensity within upper and lower bounding limits of a reference threshold value of image intensity.

The present invention also extends to a screen printing machine incorporating the above-described inspection system.

In a further aspect the present invention provides a method of inspecting deposits printed on workpieces through a printing screen, the method comprising the steps of: capturing images of at least one pair of corresponding regions of a printing screen, where comprising a body including a plurality of apertures, and a workpiece on which deposits are printed through the apertures of the printing screen; and processing the images to determine, for each of a plurality of points defining the image of the printing screen, whether the point is of aperture, and, only where the point is of aperture, determine whether the corresponding point of the corresponding image of the workpiece, as defined by a corresponding plurality of points, is of deposit, thereby enabling a determination of a print characteristic of deposits printed on the workpiece from a relationship of the points determined to be of deposit to the points determined to be of aperture.

Preferably, the images of the printing screen and the workpiece are captured simultaneously.

In one embodiment full-area images are captured of the printing screen and the workpiece.

In another embodiment line-scan images are captured of the printing screen and the workpiece.

In one embodiment the image capture and processing steps are performed simultaneously.

In another embodiment the processing step is performed subsequent to the image capture step.

In one embodiment the images of the printing screen and the workpiece are defined by respective ones of screen and workpiece signals having intensities in dependence upon the imaged features, with the points defining each of the images being time-sliced components of the respective screen and workpiece signals.

Preferably, the relationship of the points determined to be of deposit to the points determined to be of aperture is determined from a time count of a time for which the workpiece signal is determined to be of deposit relative to a time for which the screen signal is determined to be of aperture.

In another embodiment the images of the printing screen and the workpiece are pixelated images, with the points defining each of the images being pixels of the pixelated images.

Preferably, the relationship of the points determined to be of deposit to the points determined to be of aperture is determined from a number count of the number of pixels determined to be of deposit relative to the number of pixels determined to be of aperture.

In one embodiment, in the image capture step, a plurality of pairs of corresponding images of the printing screen and the workpiece are acquired at a plurality of inspection sites in accordance with an inspection schedule.

Preferably, the method further comprises the step of: performing a set-up routine to determine an inspection schedule defining a plurality of inspection sites at which images are to be acquired.

More preferably, in the set-up routine, an offset in the corresponding pair of images of the printing screen and the workpiece at each inspection site is determined, and, in determining the pixel in an image of the workpiece corresponding to a pixel in the corresponding image of the printing screen, the pixel in the image of the workpiece corresponding to the pixel in the corresponding image of the printing screen is determined in accordance with the offset.

In one embodiment the print characteristic comprises a representation of a percentage of a determined deposit coverage as compared to an expected deposit coverage.

In one embodiment the print characteristic is provided as a representation for all deposits.

Preferably, the representation is of a worst case deposit.

In another embodiment the print characteristic is provided as a plurality of representations for the inspection sites.

In one embodiment the representation for each inspection site is of a worst case deposit in the respective inspection site.

In another embodiment the representation for each inspection site comprises a plurality of representations corresponding to at least ones or groups of ones of the deposits in the respective inspection site.

Preferably, each corresponding point of the corresponding image of the workpiece is determined to be of deposit by reference to a reference threshold value of image intensity.

In one embodiment, for at least one of the apertures, each corresponding point of the corresponding image of the workpiece is determined to be of deposit in having an image intensity one of above or below a reference threshold value of image intensity.

In one embodiment, for at least one of the apertures, each corresponding point of the corresponding image of the workpiece is determined to be of deposit in having an image intensity within upper and lower bounding limits of a reference threshold value of image intensity.

Preferred embodiments of the present invention will now be described hereinbelow by way of example only with reference to the accompanying drawings, in which.

Figure 1:
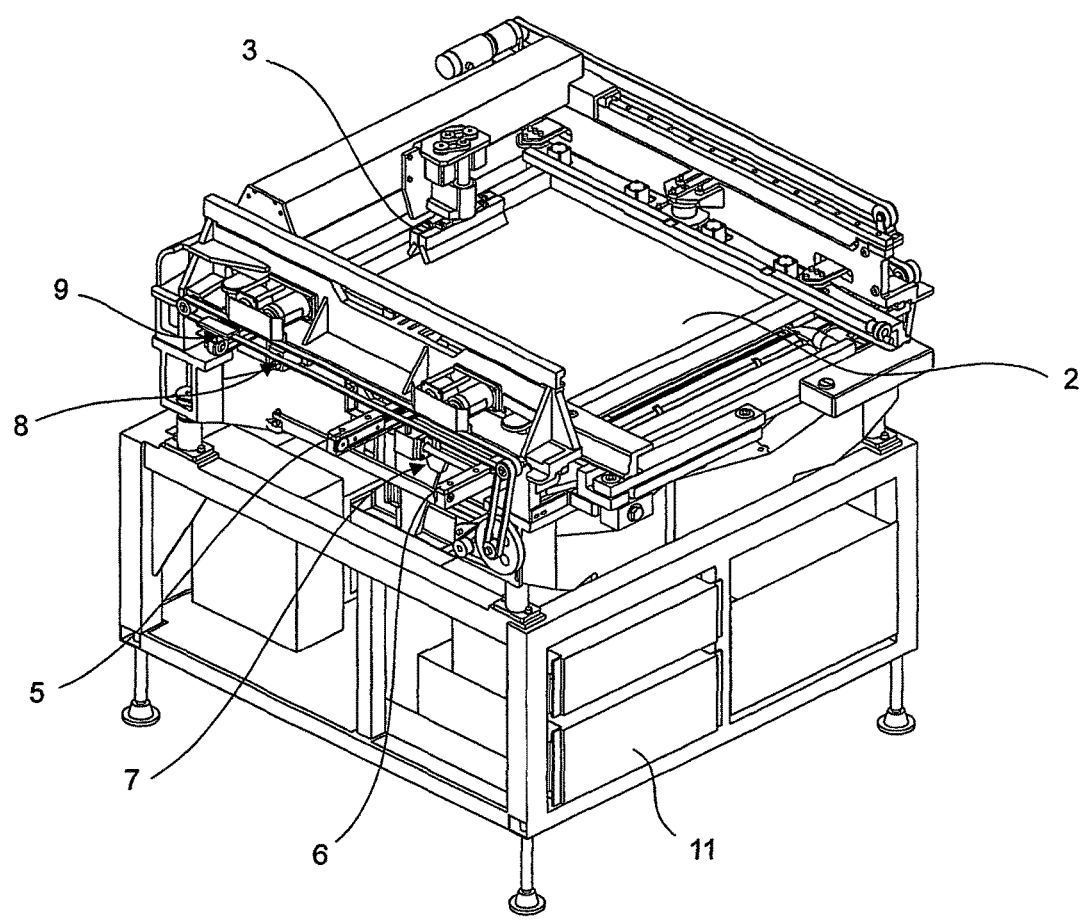
FIG. 1 illustrates a screen printing machine incorporating an inspection system in accordance with a preferred embodiment of the present invention.
Figure 3:
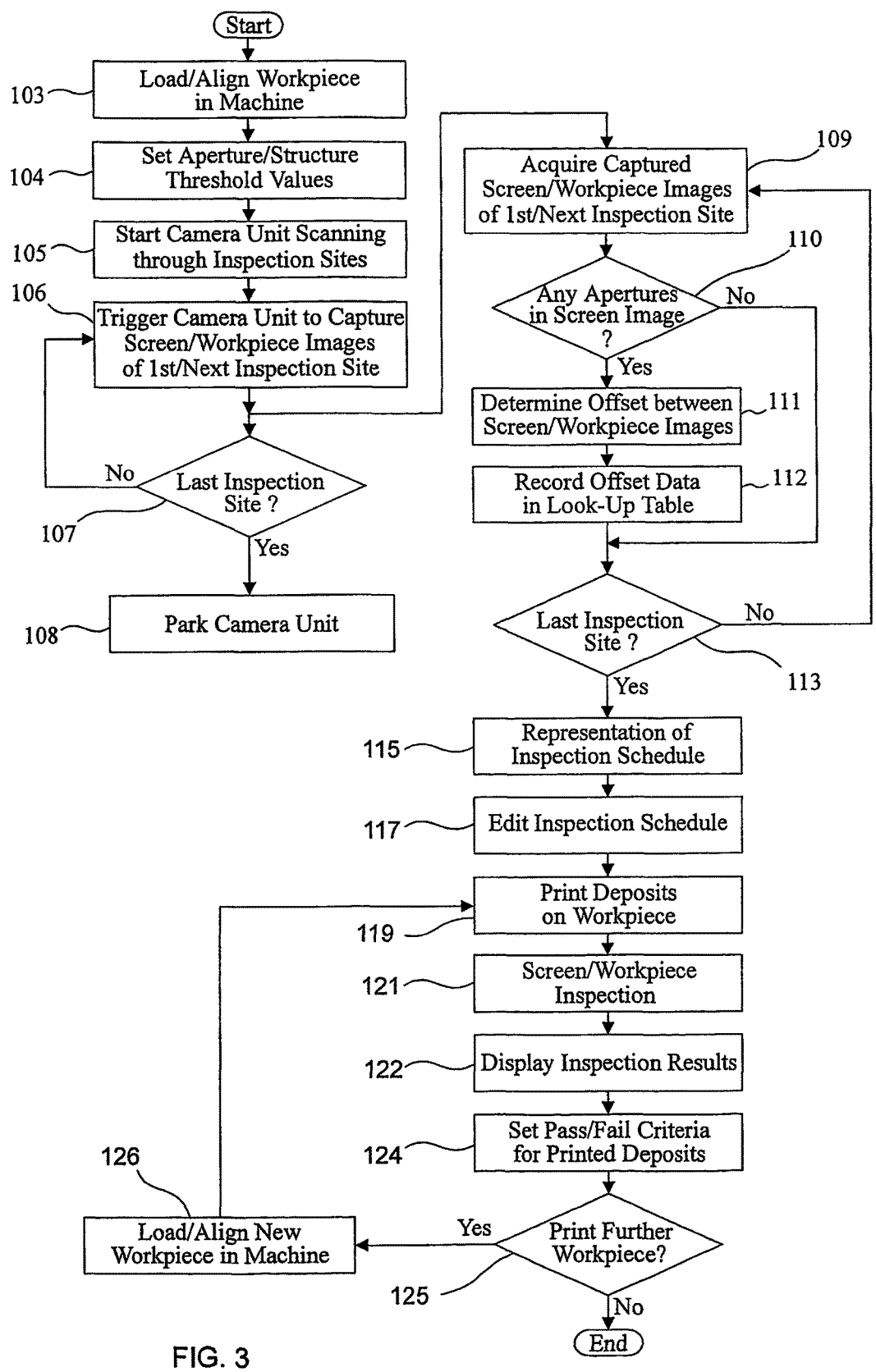
FIG. 3 illustrates a flow diagram for the set-up routine of the inspection system of the screen printing machine of FIG. 1.
Figure 4:
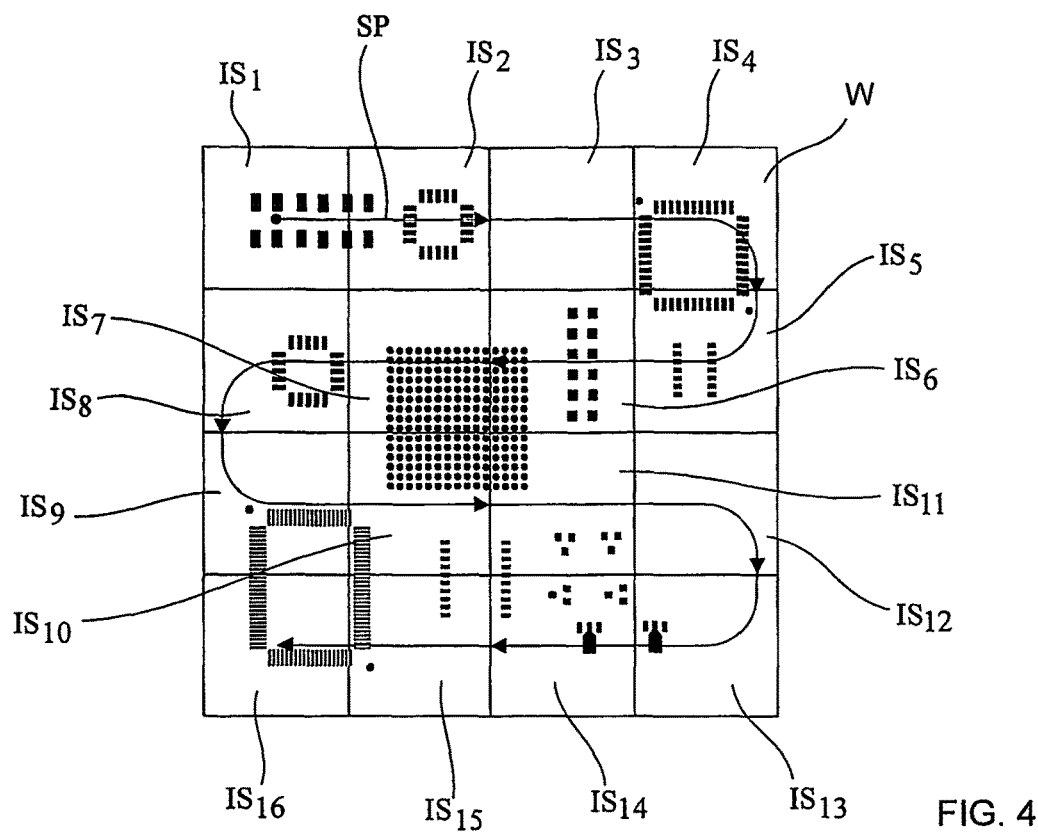
Figure 7:
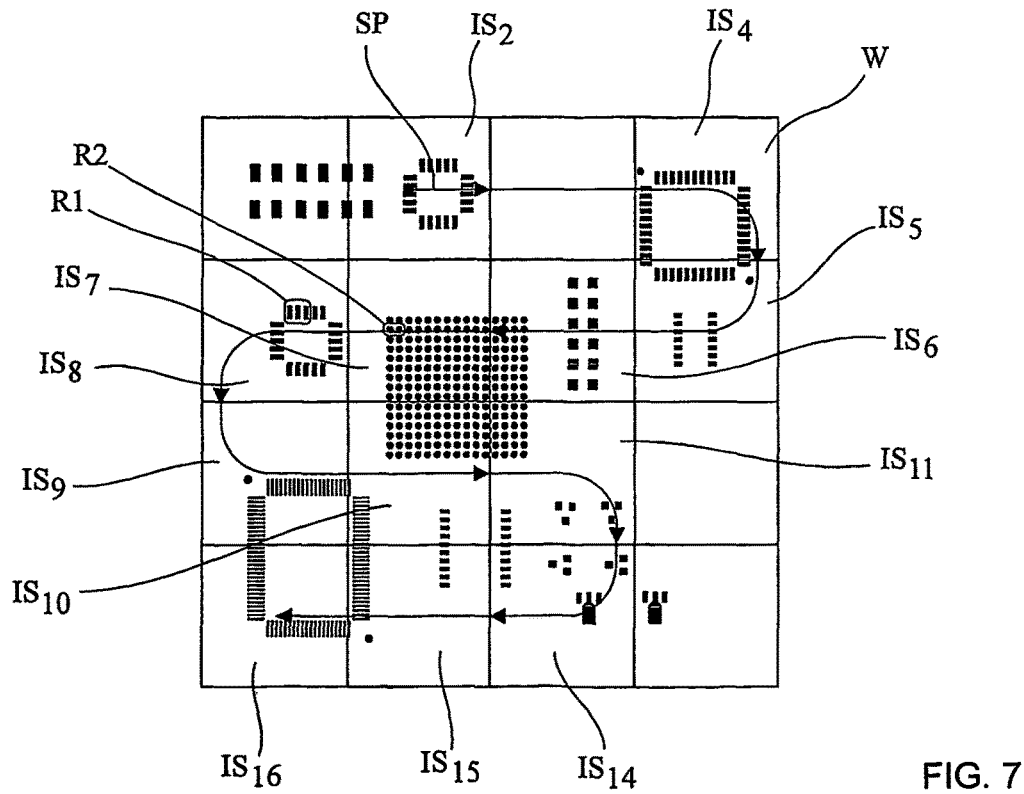
Figure 5:
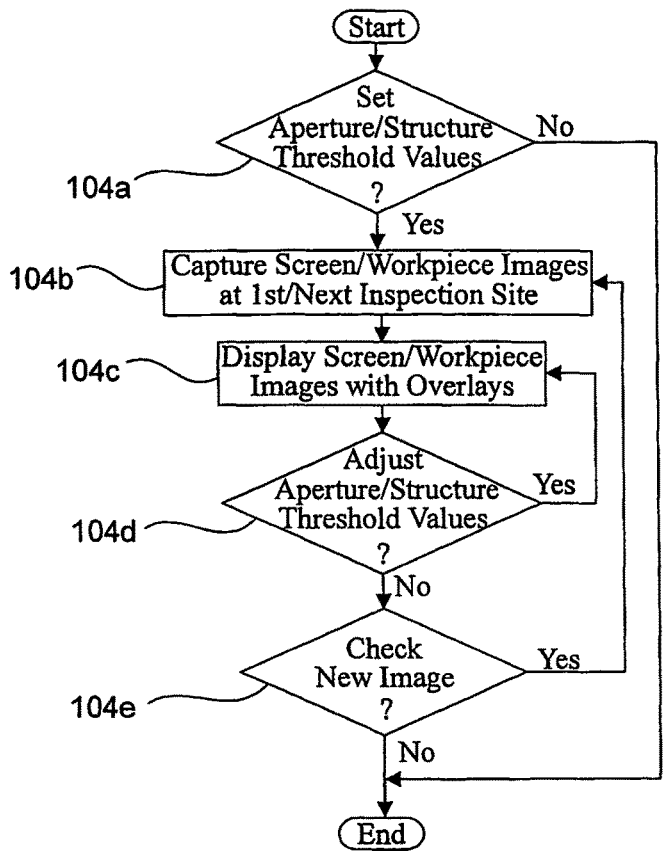
Figure 8:
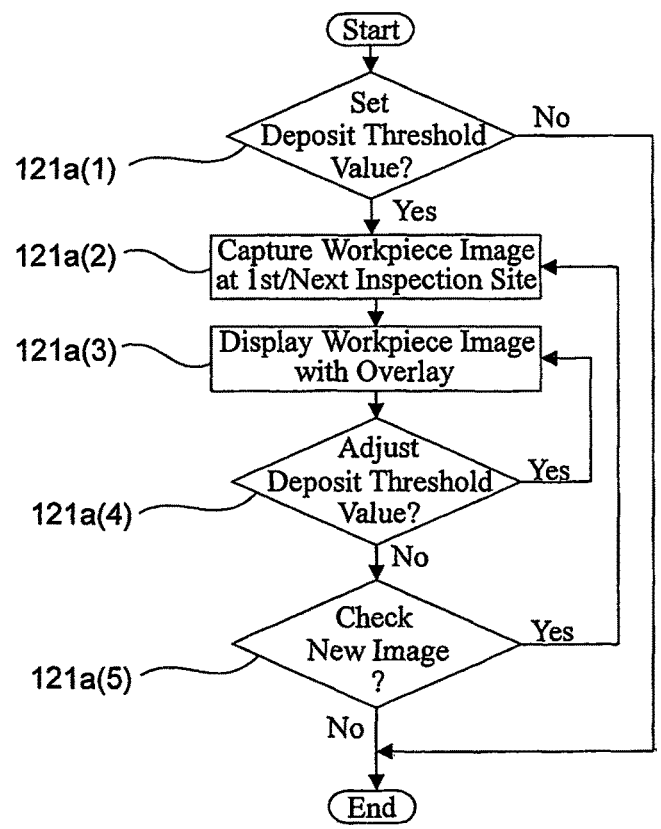
Figure 6:
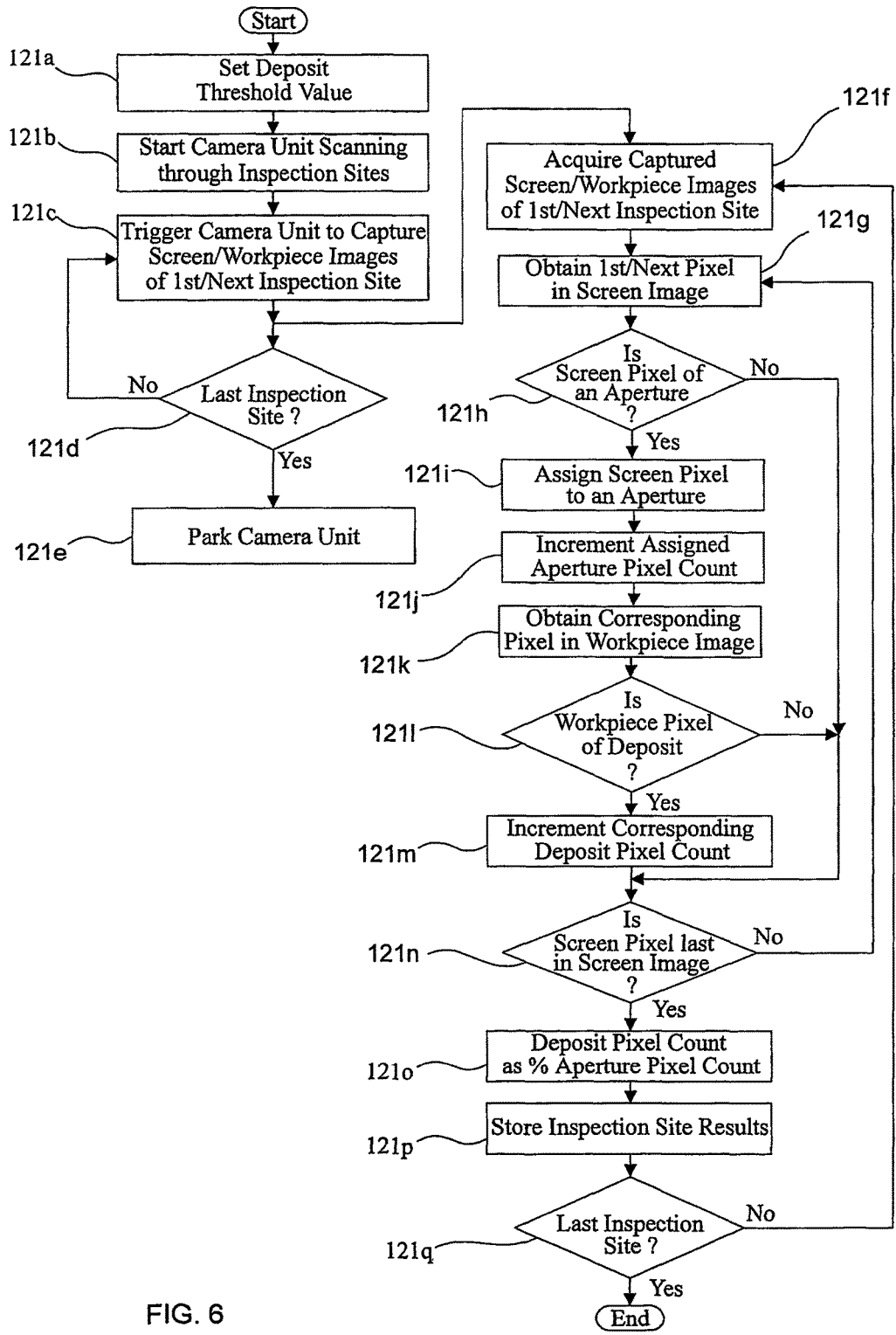
Figure 9:
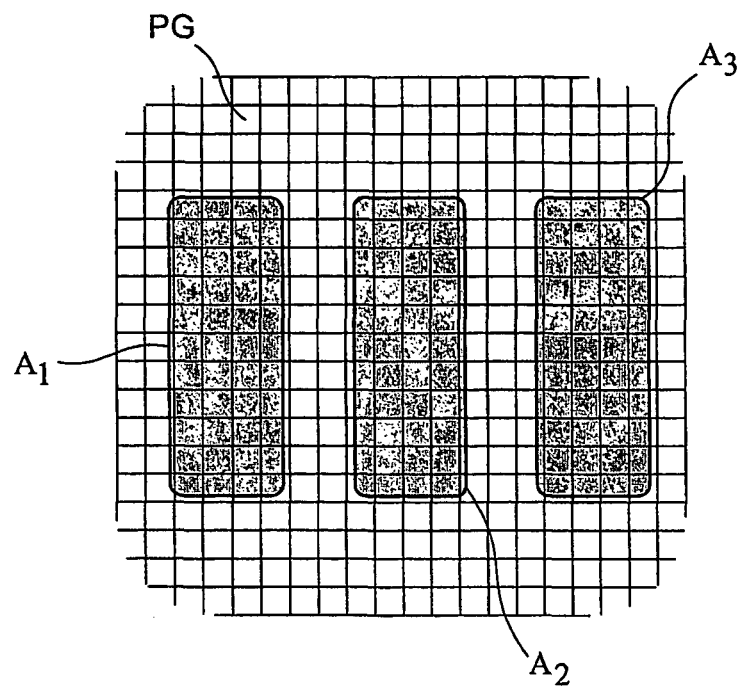
Figure 10:
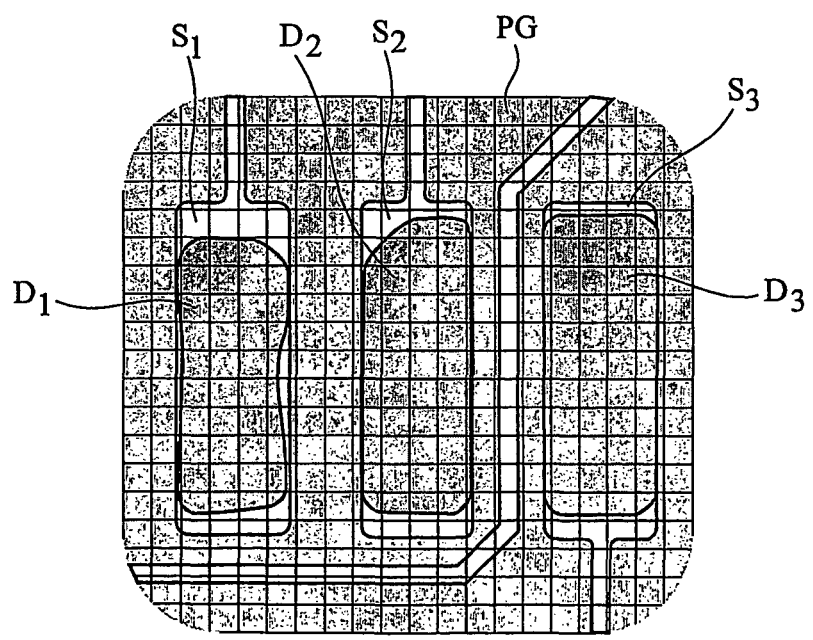
Figure 11:
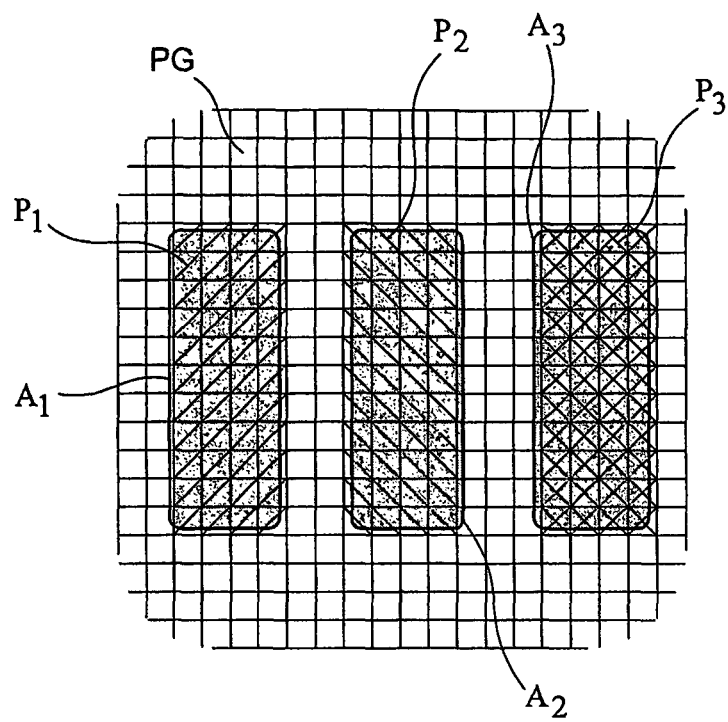
Figure 12:
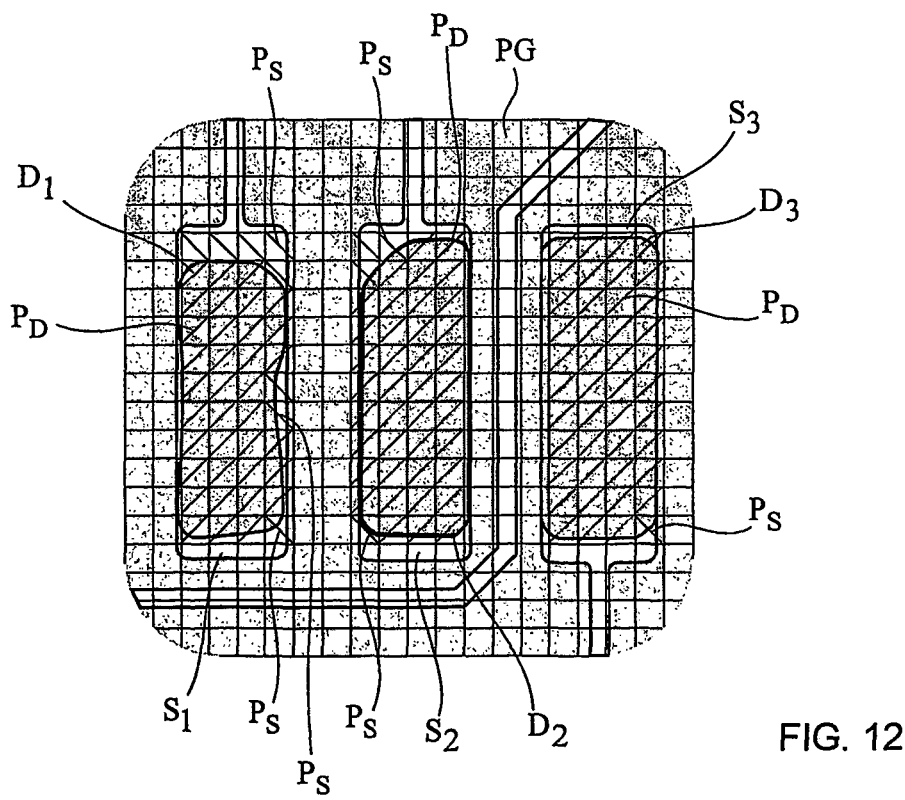
Figure 13:
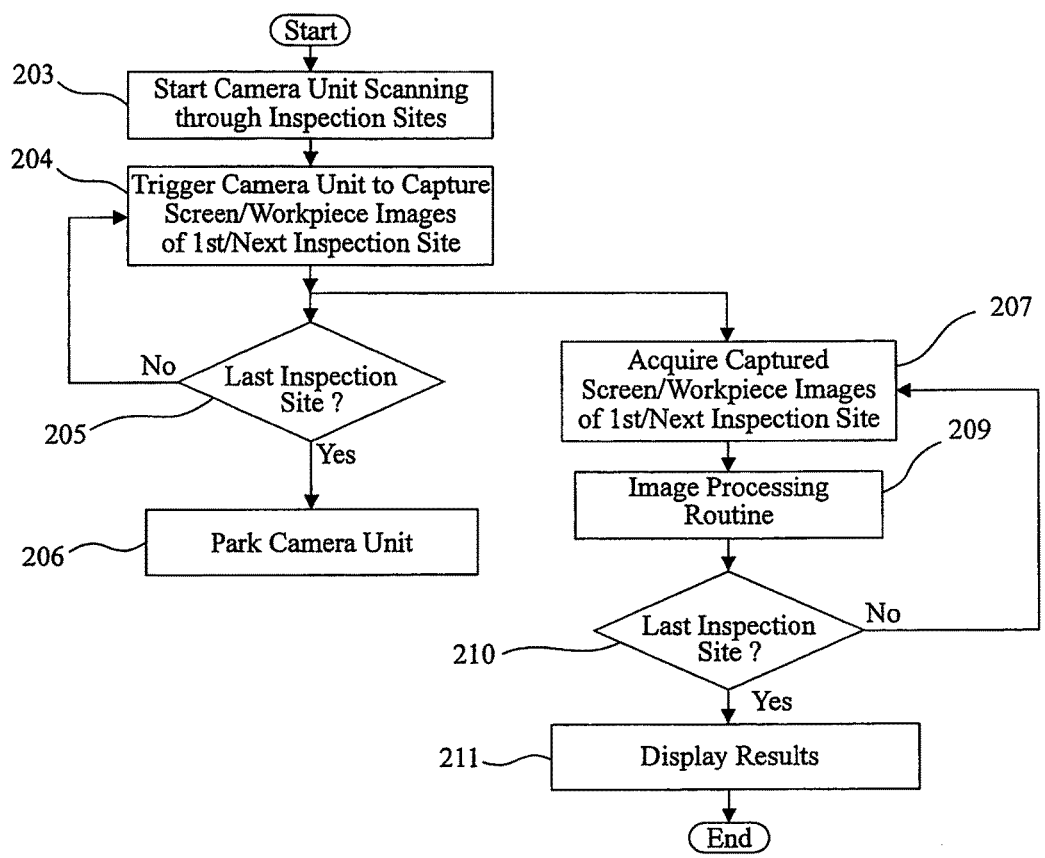
Figure 14:
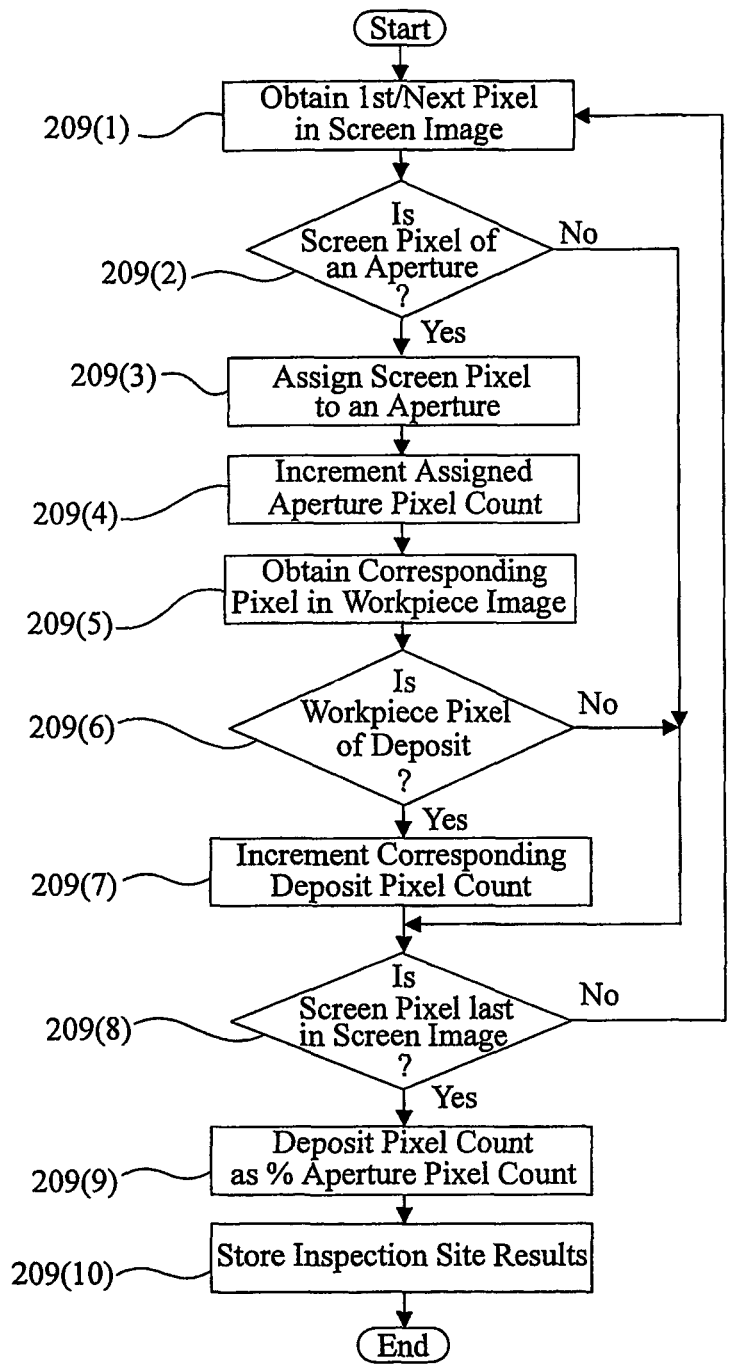
Figure 15:
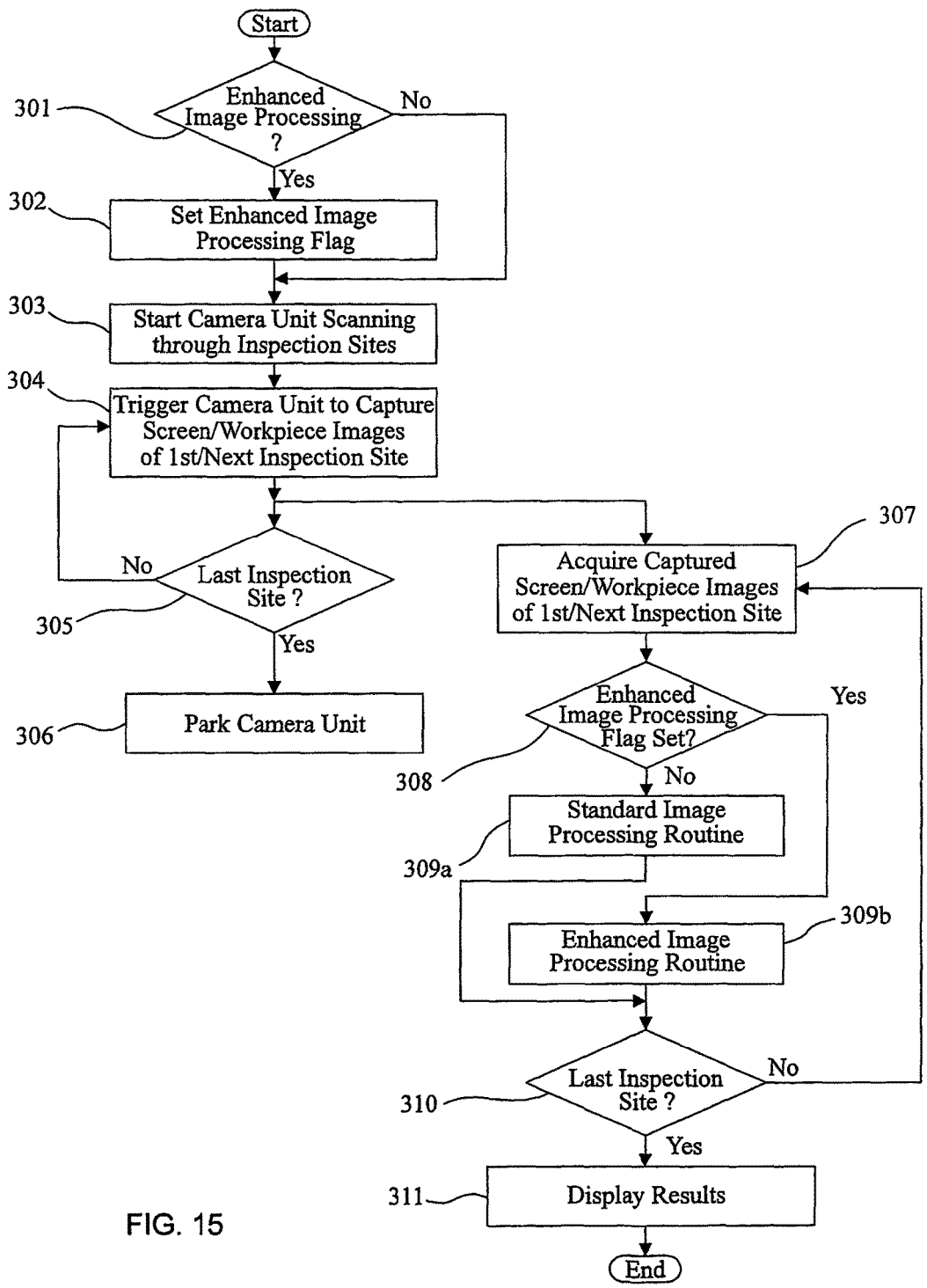
Figure 16:
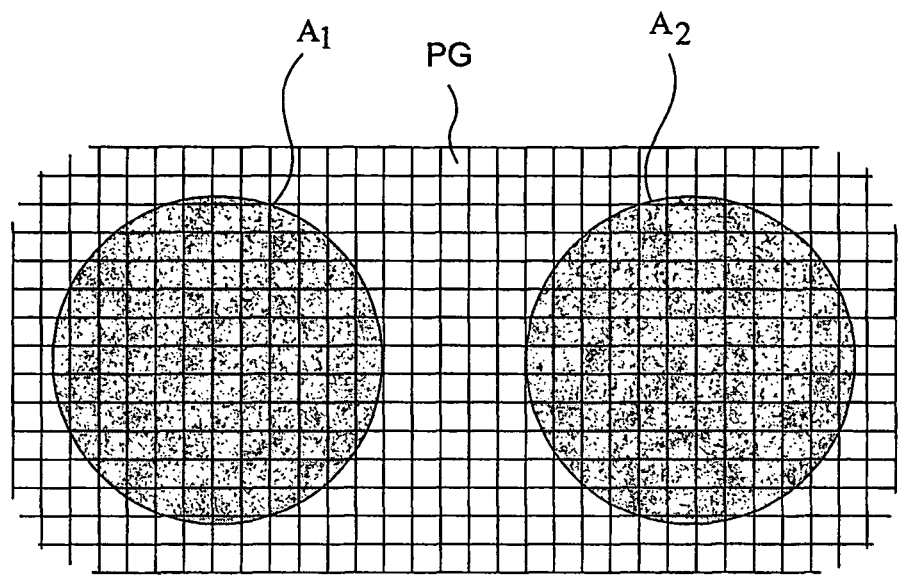
Figure 17:
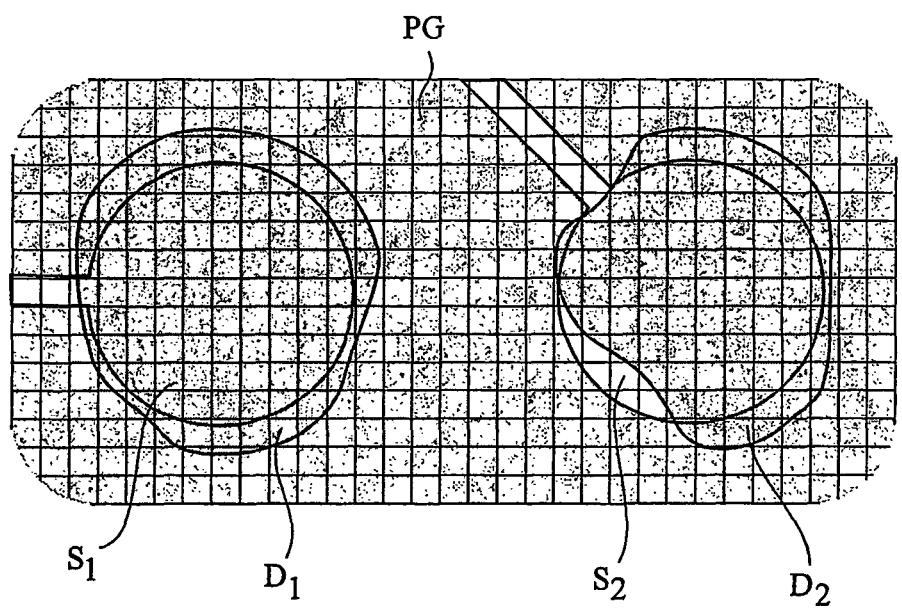
Figure 18:
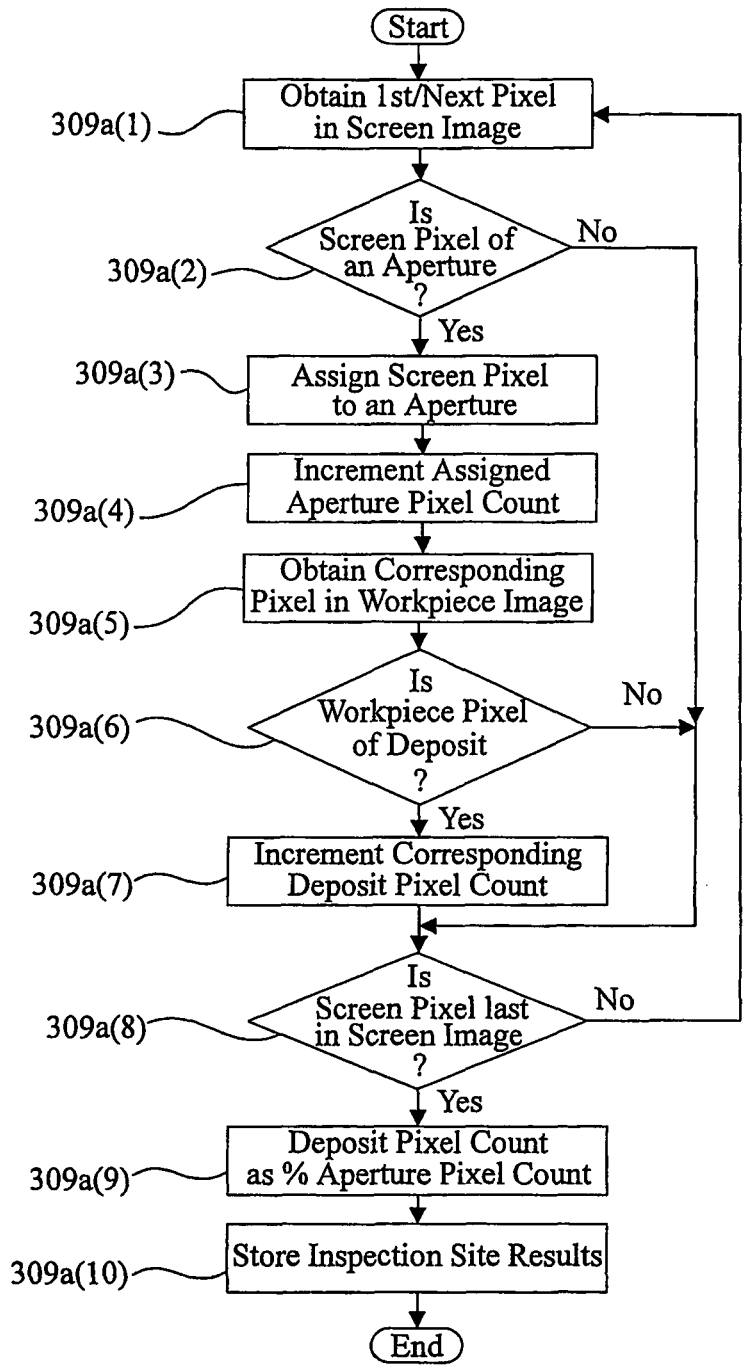
Figure 19:
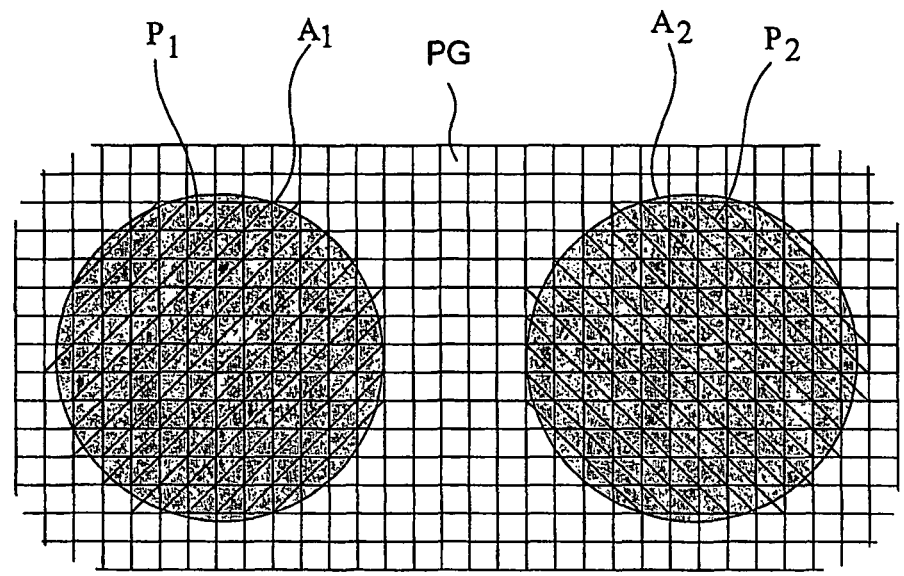
Figure 20:
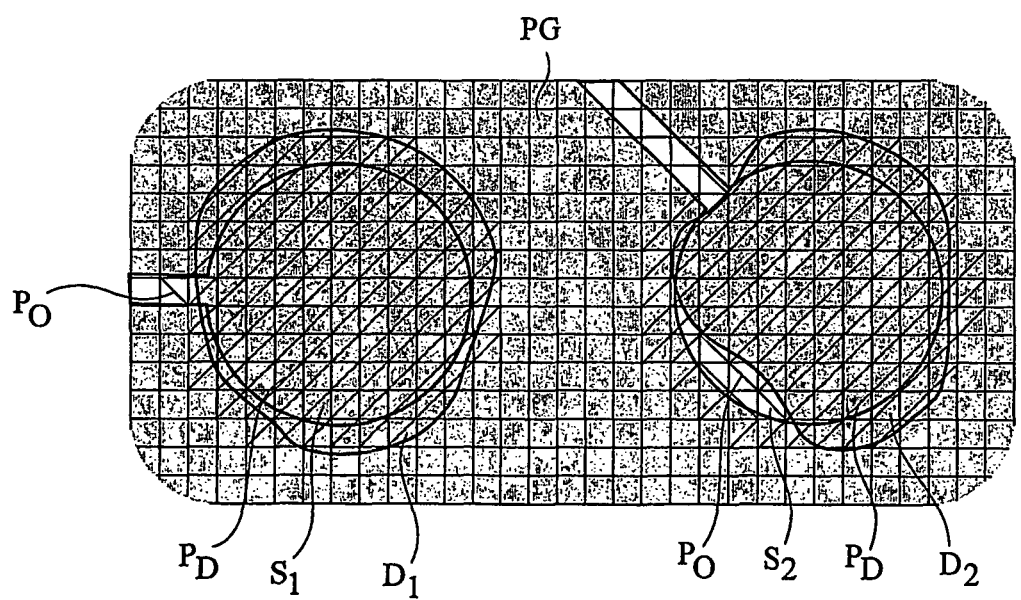
Figure 21:
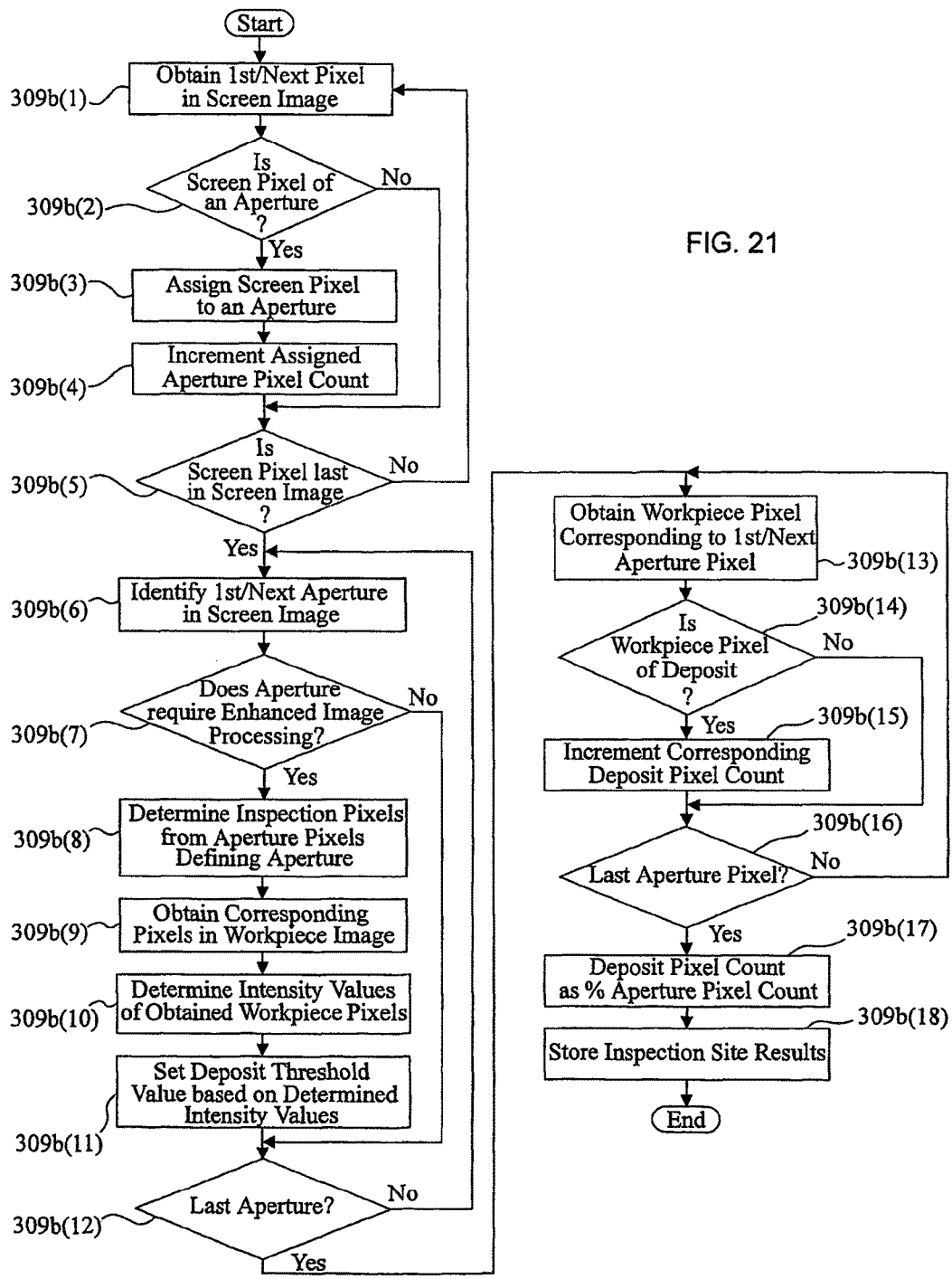
Figure 22:
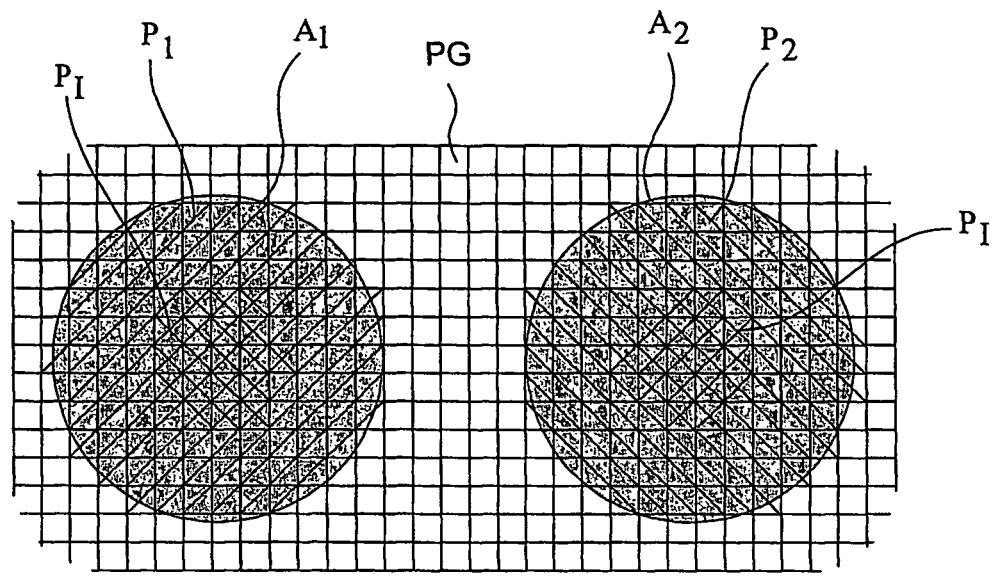
Figure 23:
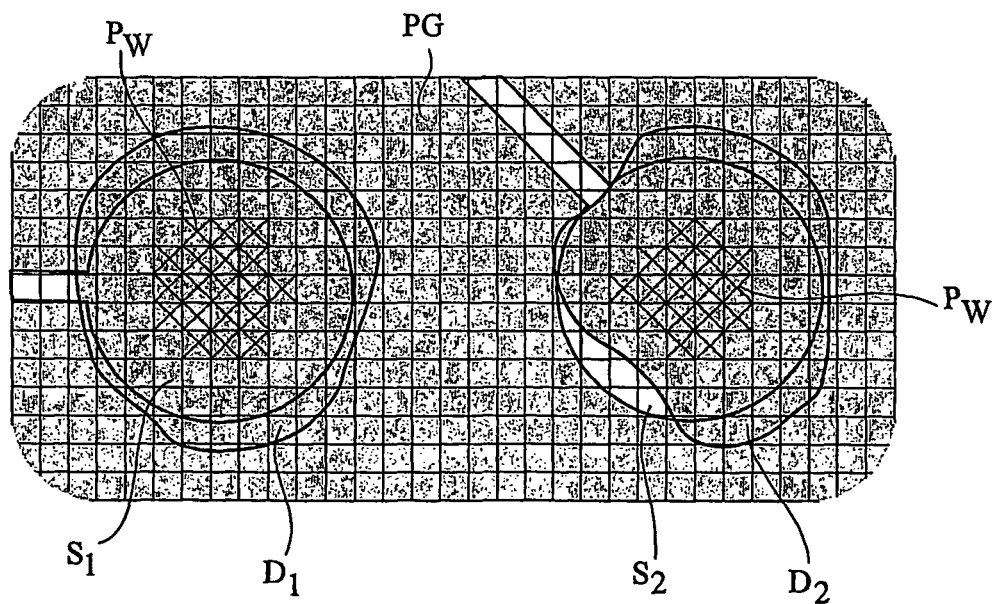
Figure 24:
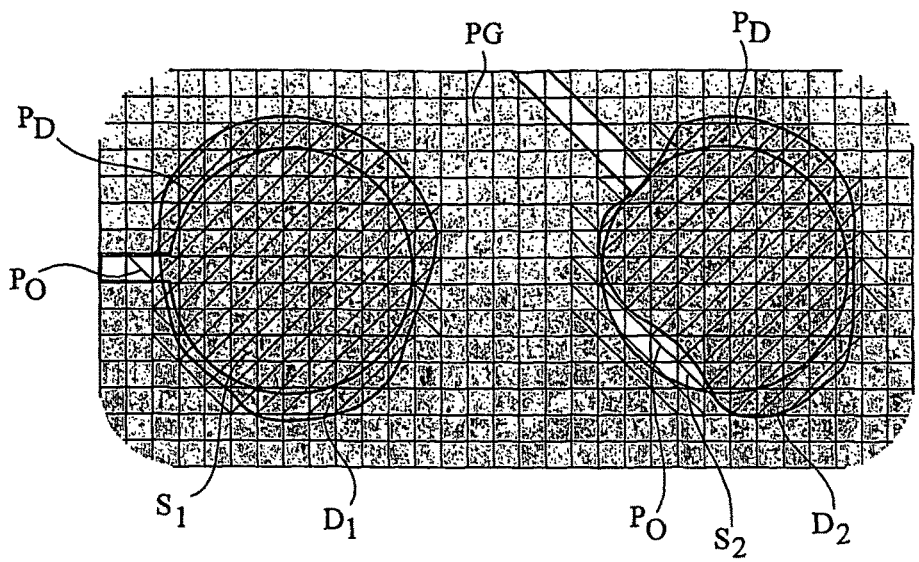
Figure 25:
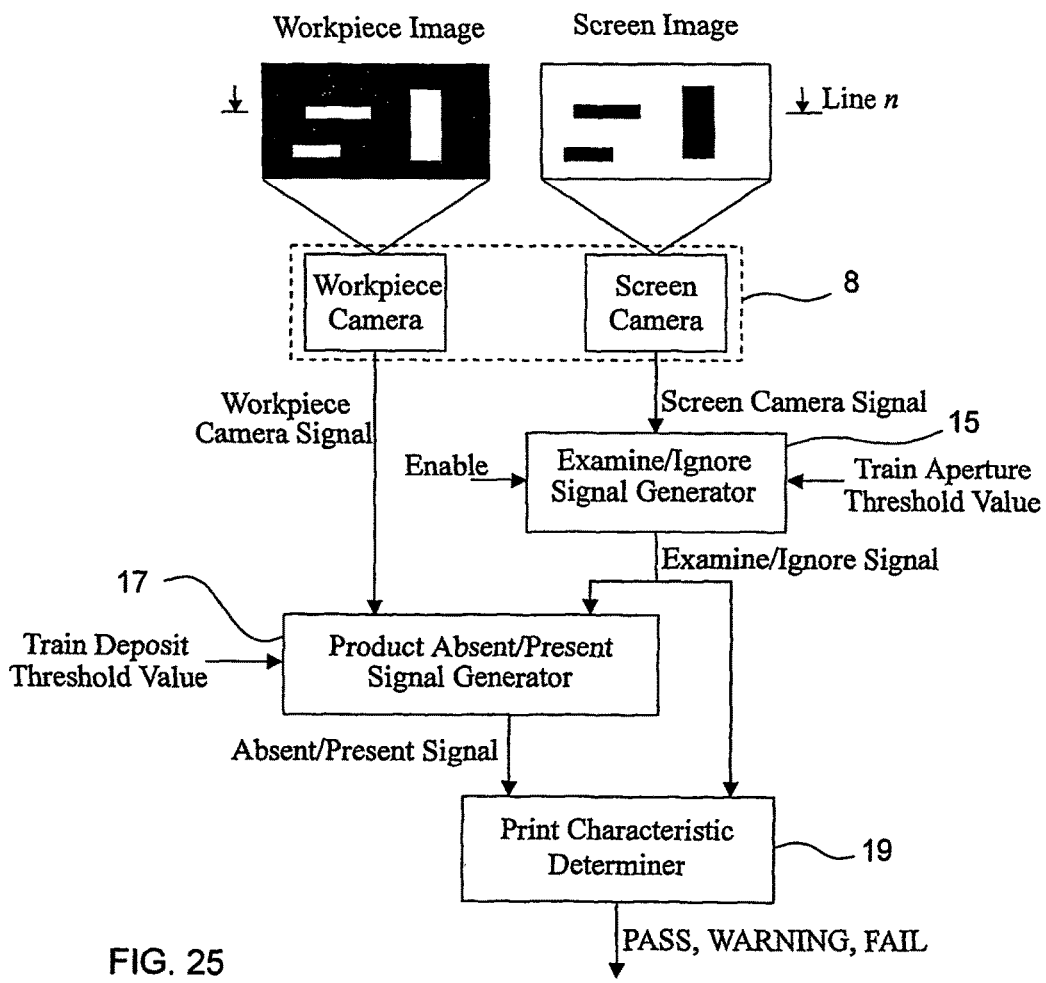
Figure 26:
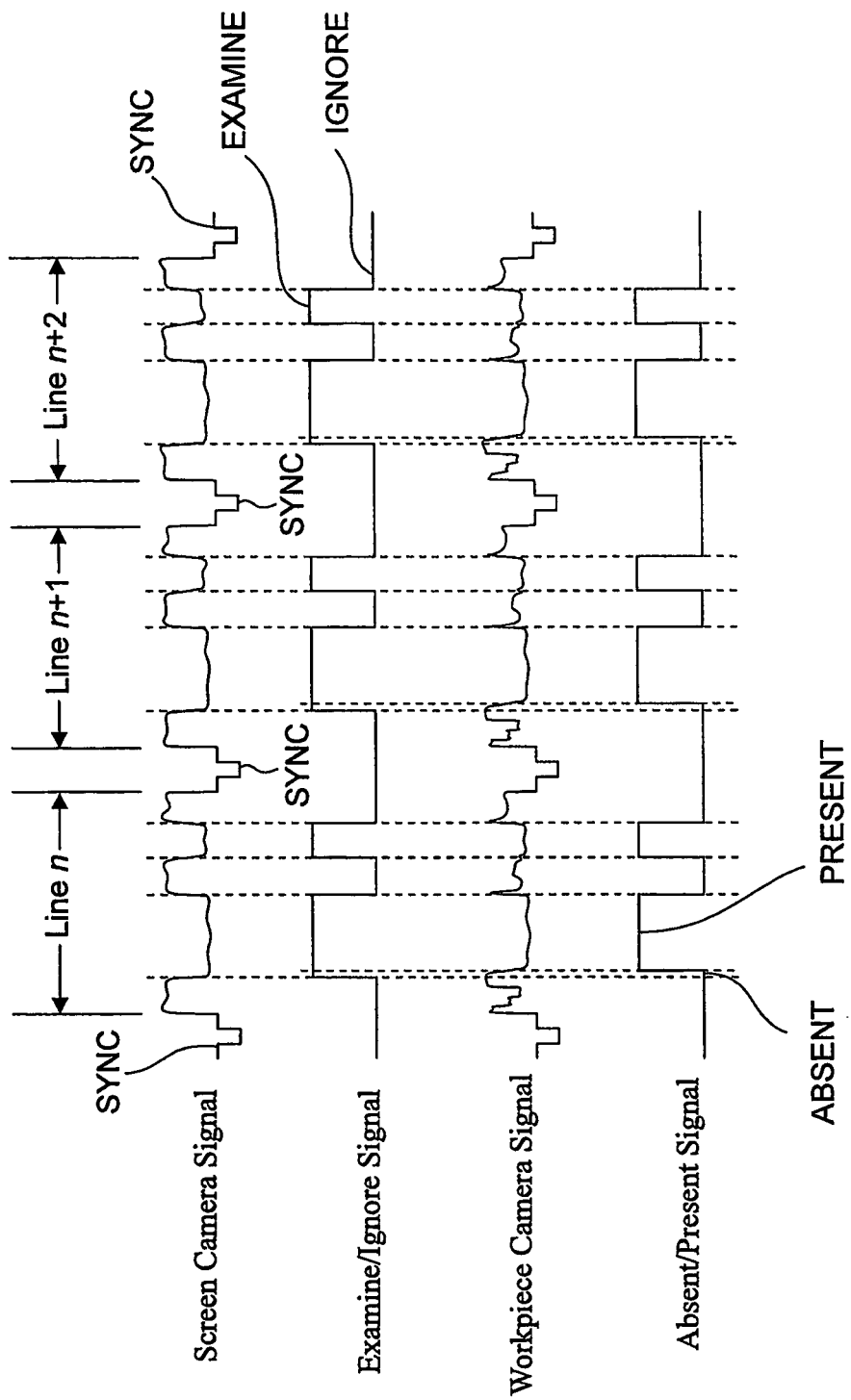

FIG. 4 diagrammatically represents a scanning path of the camera unit of the screen printing machine of FIG. 1 in the set-up routine;

FIG. 5 illustrates a flow diagram of the aperture/structure threshold value setting routine employed in the set-up routine of FIG. 3;

FIG. 6 illustrates a flow diagram of the inspection routine employed in the set-up routine of FIG. 3;

FIG. 7 diagrammatically represents a scanning path of the camera unit of the screen printing machine of FIG. 1 in an inspection routine having a defined inspection schedule;

FIG. 8 illustrates a flow diagram of the deposit threshold value setting routine employed in the inspection routine of FIG. 6;

FIG. 9 illustrates part of an acquired screen image (region R1 in FIG. 7);

FIG. 10 illustrates the part of an acquired workpiece image corresponding to the part of the screen image of FIG. 9;

FIG. 11 illustrates the screen image of FIG. 9, where identifying pixels assigned to apertures in the printing screen;

FIG. 12 illustrates the workpiece image of FIG. 10, where identifying pixels assigned to deposit and structures and counterpart to the assigned aperture pixels of FIG. 11;

FIG. 13 illustrates a flow diagram for the inspection routine of one embodiment of the inspection system of the screen printing machine of FIG. 1;

FIG. 14 illustrates a flow diagram for the image processing routine of the inspection routine of FIG. 13;

FIG. 15 illustrates a flow diagram for the inspection routine of another embodiment of the inspection system of the screen printing machine of FIG. 1;

FIG. 16 illustrates another part of an acquired screen image (region R2 in FIG. 7);

FIG. 17 illustrates the part of an acquired workpiece image corresponding to the other part of the screen image of FIG. 16;

FIG. 18 illustrates a flow diagram for a first, standard image processing routine of the inspection routine of FIG. 15;

FIG. 19 illustrates the screen image of FIG. 16, where identifying pixels assigned to apertures in the printing screen;

FIG. 20 illustrates the workpiece image of FIG. 17, where identifying pixels assigned to deposit and other than deposit and counterpart to the assigned aperture pixels of FIG. 19;

FIG. 21 illustrates a flow diagram for a second, enhanced image processing routine of the inspection routine of FIG. 15;

FIG. 22 illustrates the screen image of FIG. 19, where identifying sets of inspection pixels within the sets of aperture pixels for the respective apertures in the printing screen;

FIG. 23 illustrates the workpiece image of FIG. 20, where identifying workpiece pixels corresponding to the sets of inspection pixels in the screen image;

FIG. 24 illustrates the workpiece image of FIG. 17, where identifying pixels assigned to deposit and other than deposit and counterpart to the assigned aperture pixels of FIG. 19;

FIG. 25 illustrates a representation of an inspection circuit of an inspection system as a modification of the inspection system of the screen printing machine of FIG. 1; and FIG. 26 illustrates signals utilized in the operation of the inspection circuit of FIG. 25.

FIG. 1 illustrates a screen printing machine in accordance with a preferred embodiment of the present invention.

The screen printing machine comprises a printing screen 2 and a print head 3 which is movable back and forth across the printing screen 2 to drive printing material through a pattern of apertures in the printing screen 2 and onto a workpiece W disposed therebelow.

The screen printing machine further comprises a workpiece transport device which includes a pair of transport rails 5, 6 along which workpieces W are transported to a printing zone, and a workpiece support mechanism 7 disposed beneath the printing screen 2 to support a workpiece W at the printing zone.

The screen printing machine further comprises an inspection system which comprises a camera unit 8 for capturing images of the printing screen 2 and a workpiece W, a positioning mechanism 9, in this embodiment an X-Y table, for moving the camera unit 8 to capture images at a plurality of inspection sites, a control unit 11 for controlling the camera unit 8 and the positioning mechanism 9 to capture images of the printing screen 2 and a workpiece W and acquiring the captured images for subsequent image processing. In this embodiment the control unit 11 includes a frame grabber card for acquiring the captured images.

Figure 2:
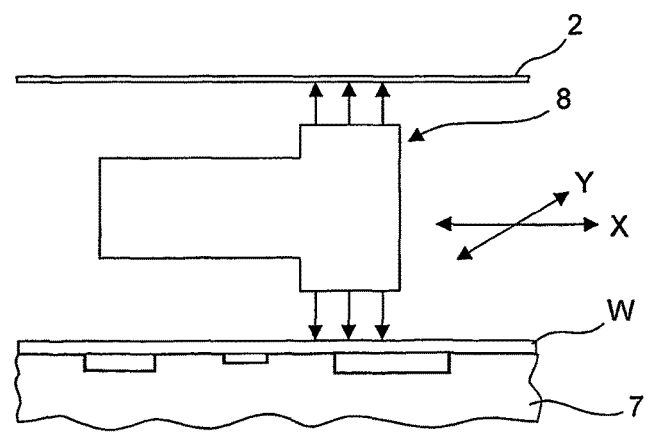
FIG. 2 illustrates a vertical elevational view of the camera unit of the screen printing machine of FIG. 1 where disposed between the printing screen and a workpiece.

Referring to FIG. 2, the camera unit 8 is configured to be moved between the printing screen 2 and a workpiece W, when at a vision height, such as to enable the simultaneous capture of corresponding pairs of images from the printing screen 2 and the workpiece W, where looking upwards at the printing screen 2 and downwards at the workpiece W, at each of the inspection sites. In this embodiment the camera unit 8 includes strobed lighting for providing for image capture on-the-fly. In this embodiment the speed of movement of the camera unit 8 is controlled such as to provide that the camera unit 8 is located at each successive inspection site at a rate which does not exceed the frame rate of the camera unit 8. In a preferred embodiment the speed of movement of the camera unit 8 is controlled such as to provide that the camera unit 8 is located at each successive inspection site in correspondence with the frame rate of the camera unit 8, but in other embodiments, where the camera unit 8 cannot be moved between certain ones of the successive inspection sites at the frame rate of the camera unit 8, for example, as a consequence of there being a relatively large distance between the inspection sites, the time of travel between those inspection sites can be greater than the frame rate of the camera unit 8.

In this embodiment a set-up routine is employed both to determine the positional relationship between the corresponding pairs of images of the printing screen 2 and the workpiece W at each of the inspection sites, and to identify those inspection sites which need to be imaged. This set-up routine is not equivalent to the learning step as employed by the inspection systems of existing screen printing machines, as no detailed image information is collected for either the printing screen 2 or the workpiece W for use in subsequent inspection, typically as to the positions and dimensions of apertures in the printing screen 2 or the positions and dimensions of structures on a workpiece W.

The set-up routine will now be described hereinbelow with reference to FIG. 3.

A workpiece W, in this embodiment a printed circuit board, is loaded into the screen printing machine and brought into alignment with the printing screen 2 (step 103).

A threshold value setting routine (step 104) is then performed to allow for the setting of respective image threshold values for images as acquired from the printing screen 2 and the workpiece W, namely, an aperture threshold value for classifying apertures in the screen image and a structure threshold value for classifying structures in the workpiece image, thereby providing for the optimization of the imaging of apertures in the printing screen 2 and structures on the workpiece W so as to avoid the possibility of not detecting such apertures or structures, as could occur where the image threshold values therefor are not properly set.

In this threshold value setting routine (step 104), the camera unit 8 is moved in stepwise fashion, starting from a starting position, typically one corner of the workpiece W, to capture corresponding pairs of images of the printing screen 2 and the workpiece W at a plurality of adjacent inspection sites. By way of representative example, FIG. 4 illustrates a plurality of adjacent inspection sites $IS_{1-16}$, in this embodiment sixteen in number, on the workpiece W.

Referring now to FIG. 5, the operator is first provided with the option as to whether to set the aperture and structure threshold values (step 104a).

Where the operator elects not to set the aperture and structure threshold values, the threshold value setting routine (step 104) is terminated.

Where the operator elects to set the aperture and structure threshold values, the threshold value setting routine (step 104) is completed.

Starting from the starting position at the first inspection site $IS_1$, the camera unit 8 captures the corresponding pair of images (step 104b) of the printing screen 2 and the workpiece W at the first inspection site $IS_1$.

The captured screen and workpiece images at the first inspection site $IS_1$, in this embodiment as acquired by the control unit 11, are then displayed together with respective ones of derived overlays superimposed thereon, where the derived overlays are of the apertures in the printing screen 2 for the screen image and the structures on the workpiece W for the workpiece image, with the derived overlays being derived initially from the acquired images using the respective ones of the existing aperture and structure threshold values (step 104c). By utilizing overlays, the operator is provided with an easily-understood representation of the derived apertures and structures as referenced to the respective actual screen and workpiece images. In a preferred embodiment the overlays are displayed as semi-transparent overlays, preferably coloured, which allow for easy identification thereof relative to the acquired images.

Where the overlays do not accurately match the respective ones of the apertures in the screen image and the structures in the workpiece image, the operator adjusts the respective ones of the aperture and structure threshold values until the desired matching is obtained (step 104d). In this embodiment the overlays are continuously re-derived with any adjustment of the aperture and structure threshold values to allow for easy setting of optimal threshold values.

The operator is then presented with the option of continuing to check the set aperture and structure threshold values in relation to the screen and workpiece images for the next, that is, second inspection site $IS_2$ (step 104e).

Where the operator elects not to check the set aperture and structure threshold values in relation to the screen and workpiece images for the second inspection site $IS_2$, the threshold value setting routine (step 104) is terminated.

Where the operator elects to check the set aperture and structure threshold values in relation to the screen and workpiece images for the second inspection site $IS_2$, the threshold value adjustment sub-routine (steps 104b to 104d) is repeated for the second inspection site $IS_2$, with the camera unit 8 being stepped to the second inspection site $IS_2$.

This process can then be repeated for each of the subsequent inspection sites $IS_{3-16}$.

Following completion of the threshold value setting routine (step 104), and from the starting position, in this embodiment the one corner of the workpiece W, scanning of the camera unit 8 over the surface of the workpiece W through the plurality of adjacent inspection sites $IS_{1-16}$ is commenced (step 105), in this embodiment in line-by-line fashion by moving the camera unit 8 laterally and advancing the camera unit 8 forwardly at a lateral edge of the workpiece W. This mode of scanning is represented in FIG. 4, where the camera unit 8 is scanned over the workpiece W along a scanning path SP and images of the workpiece W and the printing screen 2 are captured at the plurality of adjacent inspection sites $IS_{1-16}$.

When the camera unit 8 is located at the first inspection site $IS_1$, the camera unit 8 is triggered (step 106) such as to capture the corresponding pair of images of the printing screen 2 and the workpiece W at the first inspection site $IS_1$, which captured screen and workpiece images are acquired, in this embodiment by the control unit 11, and subsequently processed, as will be described in more detail hereinbelow.

A check (step 107) is then made as to whether the first inspection site $IS_1$ is the last to be inspected.

Where the first inspection site $IS_1$ is the last to be inspected, the camera unit 8 is then parked (step 108) and no further images are captured by the camera unit 8.

Where the first inspection site $IS_1$ is not the last to be inspected, the camera unit 8 is triggered (step 106) such as to capture the corresponding pair of images of the printing screen 2 and the workpiece W of the next, that is, the second inspection site $IS_2$, which captured screen and workpiece images are again acquired, in this embodiment by the control unit 11, and subsequently processed, as will be described in more detail hereinbelow.

This process is then repeated for each of the further inspection sites $IS_{2-16}$ to be inspected.

In this way, complete images of the printing screen 2 and the workpiece W are obtained, where each complete image is constructed from the images of the plurality of inspection sites $IS_{1-16}$.

In one embodiment the inspection sites $IS_{1-16}$ to be scanned in the set-up routine could be identified by the operator. Typically, the inspection sites $IS_{1-16}$ to be scanned could be selected from a graphical representation of the workpiece W or by manually moving the camera unit 8 to the required inspection sites $IS_{1-16}$.

Following capture by the camera unit 8, the pairs of images of the printing screen 2 and the workpiece W, as captured from each successive inspection site $IS_{1-16}$, are acquired (step 109) to allow for image processing.

Following acquisition of the screen and workpiece images as captured from the first inspection site $IS_1$, a check (step 110) is performed on the acquired screen image from the first inspection site $IS_1$ to determine if that screen image includes any apertures.

Where at least one aperture is present in the screen image, the position of one aperture, in this embodiment the center of a central aperture, is referenced to the position of a corresponding structure, in this embodiment a pad, on the workpiece W in the workpiece image such as to determine the offset between the screen and workpiece images (step 111). This offset data together with an identifier which identifies the first inspection site $IS_1$, typically the co-ordinates of the camera unit 8, is recorded in an offset look-up table (step 112). The provision of this offset look-up table allows for a comparison of image data for pairs of screen and workpiece images as acquired in inspection routines during printing runs, and in particular a mapping of corresponding pixels from pairs of acquired screen and workpiece images. In one embodiment, where the screen and workpiece images have differences in scale or mirror inversions, a second look-up table could be generated to allow for comparison of corresponding pixels from the screen and workpiece images.

Where no aperture is present in the screen image, the first inspection site $IS_1$ is not included in the inspection schedule, and the position-referencing and offset-recordal steps (steps 111 and 112) are skipped. In the representation of FIG. 4, the printing screen 2 includes no apertures at the third and twelfth inspection sites $IS_3$, $IS_{12}$.

A check (step 113) is then performed to determine if the first inspection site $IS_1$ is the last to be inspected.

Where the first inspection site $IS_1$ is not the last to be inspected, the image acquisition step (step 109) and the image processing sub-routine (steps 110, 111 and 112) are repeated for the next, that is, the second inspection site $IS_2$.

This process is then repeated for each of the further inspection sites $IS_{3-16}$ to be image processed.

In this embodiment the image processing performed in the image processing sub-routine (steps 110, 111 and 112) is much quicker than the image acquisition performed in the image acquisition step (step 109), which in this embodiment is completed within the frame rate of the camera unit 8, such that the image processing can be performed within the frame rate of the camera unit 8.

In this embodiment the camera unit 8 is scanned at such a rate that each successive pair of images is captured at the frame rate of the camera unit 8. For a CCIR camera format, the frame rate is 25 frames per second. At each inspection site $IS_{1-16}$, the lighting of the camera unit 8 is strobed, and the corresponding pair of images of the printing screen 2 and the workpiece W is captured by the camera unit 8 and acquired by the control unit 11.

When all of the inspection sites $IS_{1-16}$ have been acquired and image processed, a representation of the determined inspection schedule is then presented, in this embodiment through a graphic representation, to the operator (step 115), where the representation indicates the number of inspection sites $IS_{1, 2, 4-11, 13-16}$ which contain apertures and the estimated time required to perform a full inspection of all of those inspection sites $IS_{1, 2, 4-11, 13-16}$. The operator then has an opportunity to edit (step 117) the inspection schedule to omit ones of the inspection sites $IS_{1, 2, 4-11, 13-16}$ therefrom, and thereby reduce the inspection time to an acceptable level.

The screen printing machine is then operated (step 119) to print deposits, in this embodiment of printing material, here paste, on a workpiece W.

Following printing of the workpiece W, the workpiece W is separated from the printing screen 2 to a vision height, such as to allow the camera unit 8 to be scanned over the workpiece W.

An inspection routine (step 121) in accordance with the determined inspection schedule is then performed in order both to enable adjustment of the image threshold value for deposit in the acquired image of the workpiece W, namely, the deposit threshold value, and set criteria as regards the acceptability of printed deposits.

The inspection routine (step 121) will now be described hereinbelow with reference to FIG. 6.

A threshold value setting routine (step 121a) is first performed to allow for the setting of the deposit threshold value.

Referring to FIG. 7, in this threshold value setting routine (step 121a), the camera unit 8 is moved in stepwise fashion, starting from a starting position, in this embodiment the one corner of the workpiece W, to capture corresponding pairs of images of the printing screen 2 and the workpiece W at the plurality of inspection sites $IS_{2, 4-11, 14-16}$ in accordance with the determined inspection schedule. This exemplified inspection schedule provides for inspection at selected inspection sites $IS_{2, 4-11, 14-16}$, with the first, third, twelfth and thirteenth inspection sites $IS_1$, $IS_3$, $IS_{12}$, $IS_{13}$ being omitted from the inspection schedule. The third and twelfth inspection sites $IS_3$, $IS_{12}$ inspected in the set-up routine have been omitted from the inspection schedule as those inspection sites do not include any apertures in the printing screen 2 and hence deposits on the workpiece W, and the first and thirteenth inspection sites $IS_1$, $IS_{13}$ inspected in the set-up routine have been omitted from the inspection schedule in order to reduce the required processing, these inspection sites only including relatively large apertures in the printing screen 2 which do not ordinarily lead to problems in the printing of deposits on workpieces W.

Referring to FIG. 8, the operator is first provided with the option as to whether to set the deposit threshold value (step 121a(1)).

Where the operator elects not to set the deposit threshold value, the threshold value setting routine (step 121a) is terminated.

Where the operator elects to set the deposit threshold value, the threshold value setting routine (step 121a) is completed.

Starting from the starting position at the second inspection site $IS_2$, the camera unit 8 captures the image of the workpiece W at the second inspection site $IS_2$ (step 121a(2)).

The captured workpiece image at the second inspection site $IS_2$, in this embodiment as acquired by the control unit 11, is then displayed together with a derived overlay of the deposits on the workpiece W superimposed thereon, where the derived overlay is derived initially from the acquired workpiece image using the existing deposit threshold value (step 121a(3)). As mentioned hereinabove, by utilizing an overlay, the operator is provided with an easily-understood representation of the derived deposits as referenced to the deposits in the actual workpiece image. In a preferred embodiment the overlay is displayed as a semi-transparent overlay, preferably coloured, which allows for easy identification thereof relative to the acquired image.

Where the overlay does not accurately match the deposits in the workpiece image, the operator adjusts the deposit threshold value (step 121*a*(4)) until a more optimal matching is obtained. In this embodiment the overlay is continuously re-derived with any adjustment of the deposit threshold value to allow for easy setting of an optimal deposit threshold value.

The operator is then presented with the option of continuing to check the set deposit threshold value in relation to the workpiece image for the next, in this embodiment fourth inspection site $IS_4$ in accordance with the inspection schedule (step 121*a*(5)).

Where the operator elects not to check the set deposit threshold value in relation to the workpiece image for the fourth inspection site $IS_4$, the threshold value setting routine (121*a*) is terminated.

Where the operator elects to check the set deposit threshold value in relation to the workpiece image for the fourth inspection site $IS_4$, the threshold value adjustment sub-routine (steps 121*a*(2-4)) is repeated for the fourth inspection site $IS_4$, with the camera unit 8 being stepped to the fourth inspection site $IS_4$.

This process can then be repeated for each of the subsequent inspection sites $IS_{5-11,\ 14-16}$.

Following completion of the threshold value setting routine (step 121*a*), and from the starting position as defined by the inspection schedule, in this embodiment the second inspection site $IS_2$, scanning of the camera unit 8 over the surface of the workpiece W, in this embodiment in line-by-line fashion by moving the camera unit 8 laterally and advancing the camera unit 8 forwardly at a lateral edge of the workpiece W, is commenced, such as successively to capture corresponding pairs of images of the printing screen 2 and the workpiece W at the plurality of inspection sites $IS_{2,\ 4-11,\ 14-16}$ in accordance with the inspection schedule (step 121*b*). Reference is again made to FIG. 7 which represents this mode of scanning, where the camera unit 8 is scanned over the workpiece W along a scanning path SP and images of the printing screen 2 and the workpiece W are captured at the plurality of inspection sites $IS_{2,\ 4-11,\ 14-16}$ in accordance with the inspection schedule.

In this embodiment, where the camera unit 8 has strobed lighting for image capture on-the-fly, the speed of movement of the camera unit 8 is controlled to provide that the camera unit 8 is located at each successive inspection site $IS_{2,\ 4-11,\ 14-16}$, as defined by the inspection schedule, in correspondence with the frame rate of the camera unit 8, with the camera unit 8 being accelerated as necessary, for example, between the second and fourth inspection sites $IS_2$, $IS_4$ which are not adjacent.

When the camera unit 8 is located at the second inspection site $IS_2$, the camera unit 8 is triggered (step 121*c*) such as to capture the corresponding pair of images of the printing screen 2 and the workpiece W at the second inspection site $IS_2$, which captured screen and workpiece images are acquired, in this embodiment by the control unit 11, and subsequently processed, as will be described in more detail hereinbelow.

A check (step 121*d*) is then made as to whether the second inspection site $IS_2$ is the last to be inspected.

Where the second inspection site $IS_2$ is the last to be inspected, the camera unit 8 is then parked (step 121*e*) and no further images are captured by the camera unit 8.

Where the second inspection site $IS_2$ is not the last to be inspected, the camera unit 8 is triggered (step 121*c*) such as to capture the corresponding pair of images of the printing screen 2 and the workpiece W of the next, in this embodiment fourth inspection site $IS_2$, which captured screen and workpiece images are again acquired, in this embodiment by the control unit 11, and subsequently processed, as will be described in more detail hereinbelow.

This process is then repeated for each of the further inspection sites $IS_{5-11,14-16}$ to be inspected in accordance with the inspection schedule.

Following capture by the camera unit 8, the pairs of images of the printing screen 2 and the workpiece W, as captured from each successive inspection site $IS_{2,\ 4-11,\ 14-16}$, are acquired (step 121*f*) to allow for image processing.

In this embodiment the acquired screen and workpiece images are pixelated and defined by a pixel grid PG. FIGS. 9 and 10 illustrate respective corresponding parts (region R1 in FIG. 7) of the acquired screen and workpiece images, each having the same pixel grid PG. For ease of illustration, the pixel grid PG is illustrated as having a very coarse resolution, whereas, in practice, the resolution of the pixel grid PG would be much finer, such as to minimize any error introduced by edge effects, as will be described in more detail hereinbelow.

FIG. 9 illustrates a part (region R1 in FIG. 7) of the acquired screen image, where encompassing three equi-sized, rectangular apertures $A_1$, $A_2$, $A_3$.

FIG. 10 illustrates the corresponding part (region R1 in FIG. 7) of the corresponding acquired workpiece image, where encompassing three equi-sized rectangular structures $S_1$, $S_2$, $S_3$ having deposits $D_1$, $D_2$, $D_3$ printed thereon.

Following acquisition of the pair of screen and workpiece images as captured from the second inspection site $IS_2$, a first pixel of the screen image is obtained from the image data (step 121*g*), and checked (step 121*h*) to classify the screen pixel as corresponding to the body of the printing screen 2, in this embodiment as characterized by a light pixel having an intensity above the set aperture threshold value, or an aperture, in this embodiment as characterized by a dark pixel having an intensity below the set aperture threshold value.

In an alternative embodiment, with a different lighting arrangement, the body of the printing screen 2 could be characterized by dark pixels and the apertures of the printing screen 2 characterized by light pixels. In this embodiment the checking step (step 121*h*) would classify the screen pixel as being of an aperture where the pixel has an intensity above the set aperture threshold value.

Where the screen pixel is classified as being of an aperture, namely, an aperture pixel, the screen pixel is assigned to an aperture (step 121*i*), a pixel count for that aperture is incremented (step 121*j*), and the corresponding pixel from the workpiece image, in this embodiment as mapped by utilizing the offset look-up table, is obtained (step 121*k*).

For the purposes of exemplification, FIG. 11 illustrates the same screen image as that of FIG. 9, where the pixels $P_1$, $P_2$, $P_3$ assigned to each of the respective apertures $A_1$, $A_2$, $A_3$ are identified. For the purposes of representation, the pixels $P_1$ of the first aperture $A_1$ are designated by a forward slash, the pixels $P_2$ of the second aperture $A_2$ are designated by a backward slash, and the pixels $P_3$ of the third aperture $A_3$ are designated by a cross.

The obtained workpiece pixel is then checked (step 121*l*) to determine if that workpiece pixel corresponds to deposit, in this embodiment as characterized by a dark pixel having an intensity below the set deposit threshold value.

In an alternative embodiment, with a different lighting arrangement, deposit could be characterized by light pixels. In this embodiment the checking step (step 121*l*) would classify a workpiece pixel as corresponding to deposit where having an intensity above the set deposit threshold value.

Where the workpiece pixel is classified as being of deposit, a deposit pixel count, which is a counterpart to the aperture pixel count, is incremented (step 121m).

For the purposes of exemplification, FIG. 12 illustrates the same workpiece image as that of FIG. 10, where the counterpart pixels $P_D$ classified as being of deposit $D_1$, $D_2$, $D_3$ are designated by a forward slash and the counterpart pixels $P_S$ classified as being of one of the structures $S_1$, $S_2$, $S_3$ are designated by a backward slash. As will be noted, pixels can encompass one or a combination of deposit, a structure on the workpiece W or the body of the workpiece W. Where a combination of such features is encompassed by a pixel, the intensity of that pixel corresponds to the relative fractions of the respective features, and thus the relative fraction of deposit within a pixel which is required to classify that pixel as being of deposit is determined by the set deposit threshold value. As mentioned hereinabove, the resolution of the pixel grid PG is illustrated as having a particularly coarse resolution merely for the purposes of ease of illustration. In practice, the pixel grid PG will normally be of such a resolution that any mis-classification of edge pixels will have only a very minor effect in the determination of percentage of deposit coverage.

Subsequently, or where the screen pixel is not classified as being of an aperture in the screen pixel checking step (step 121h), a check (step 121n) is made as to whether the screen pixel is the last pixel in the screen image.

Where the screen pixel is not the last pixel in the screen image, the next screen pixel is obtained (step 121g) from the screen image, and the above-described pixel classification sub-routine (steps 121h-m) is repeated.

Where the screen pixel is the last pixel in the screen image, then, for each aperture, the percentage of deposit coverage is determined (step 121o) from the deposit pixel count as referenced to the aperture pixel count.

The determined percentages are then stored for the second inspection site $IS_2$ (step 121p).

A check (step 121q) is then made as to whether the second inspection site $IS_2$ is the last to be inspected.

Where the second inspection site $IS_2$ is not the last to be inspected, the image acquisition step (step 121f) and the image processing sub-routine (steps 121g-p) are repeated for the next, in this embodiment fourth inspection site $IS_4$.

This process is then repeated for each of the further inspection sites $IS_{5-11, 14-16}$ to be image processed as defined by the inspection schedule.

Following completion of the inspection routine (step 121), the inspection results, as percentages of deposit coverage where determined by reference to respective apertures, are displayed (step 122). The inspection results can be presented in many different ways, depending upon the requirements of the operator. In one embodiment only the percentage coverage for the worst case deposit for all of the inspection sites $IS_{2, 4-11, 14-16}$ could be displayed. In another embodiment the percentage coverage for the worst case deposit for each of the inspection sites $IS_{2, 4-11, 14-16}$ could be displayed. In a further embodiment the percentage coverage for selected deposits for the inspection sites $IS_{2, 4-11, 14-16}$ could be displayed.

The operator is then prompted to set the pass/fail criteria for printed deposits (step 124), which can be a single, global value for all deposits of all of the inspection sites $IS_{2, 4-11, 14-16}$, an individual value for deposits of each of the inspection sites $IS_{2, 4-11, 14-16}$, or an individual value for selected deposits of the inspection sites $IS_{2, 4-11, 14-16}$.

The operator is then provided with the option (step 125) of printing a further workpiece W.

Where the operator elects to print a further workpiece W, another workpiece W is loaded and brought into alignment in the screen printing machine (step 126), and the printing, inspection, result display and criteria-setting steps (steps 119 to 124) are repeated.

Where the operator elects not to print a further workpiece W, the set-up routine is terminated.

In one alternative embodiment, where the offset in the screen and workpiece images is sufficiently small as not significantly to affect the inspection results, the set-up routine need not provide for determination of the offset in the screen and workpiece images.

In another alternative embodiment, where the inspection schedule is determined manually by the operator, the set-up routine could be omitted.

In operation of the screen printing machine, the inspection system provides for characterization of the deposits printed on workpieces W through the application of an inspection routine.

One embodiment of the inspection routine will now be described hereinbelow with reference to FIG. 13.

Following the loading of a workpiece W, alignment and printing of the workpiece W, and separation of the workpiece W from the printing screen 2 to a vision height, and from the starting position as defined by the inspection schedule, in this embodiment the second inspection site $IS_2$, scanning of the camera unit 8 over the surface of the workpiece W, in this embodiment in line-by-line fashion by moving the camera unit 8 laterally and advancing the camera unit 8 forwardly at a lateral edge of the workpiece W, is commenced, such as successively to capture corresponding pairs of images of the printing screen 2 and the workpiece W at the plurality of inspection sites $IS_{2, 4-11, 14-16}$ in accordance with the inspection schedule (step 203). Reference is again made to FIG. 7 which represents this mode of scanning, where the camera unit 8 is scanned over the workpiece W along a scanning path SP and images of the printing screen 2 and the workpiece W are captured at the plurality of inspection sites $IS_{2, 4-11, 14-16}$ in accordance with the inspection schedule.

In this embodiment, where the camera unit 8 has strobed lighting for image capture on-the-fly, the speed of movement of the camera unit 8 is controlled to provide that the camera unit 8 is located at each successive inspection site $IS_{2, 4-11, 14-16}$, as defined by the inspection schedule, in correspondence with the frame rate of the camera unit 8, with the camera unit 8 being accelerated as necessary, for example, between the second and fourth inspection sites $IS_2$, $IS_4$ which are not adjacent.

When the camera unit 8 is located at the second inspection site $IS_2$, the camera unit 8 is triggered (step 204) such as to capture the corresponding pair of images of the printing screen 2 and the workpiece W at the second inspection site $IS_2$, which captured screen and workpiece images are acquired, in this embodiment by the control unit 11, and subsequently processed, as will be described in more detail hereinbelow.

A check (step 205) is then made as to whether the second inspection site $IS_2$ is the last to be inspected.

Where the second inspection site $IS_2$ is the last to be inspected, the camera unit 8 is then parked (step 206) and no further images are captured by the camera unit 8.

Where the second inspection site $IS_2$ is not the last to be inspected, the camera unit 8 is triggered (step 204) such as to capture the corresponding pair of images of the printing screen 2 and the workpiece W of the next, in this embodiment fourth inspection site $IS_4$, which captured screen and workpiece images are again acquired, in this embodiment by the control unit 11, and subsequently processed, as will be described in more detail hereinbelow.

This process is then repeated for each of the further inspection sites $IS_{5\text{-}11, 14\text{-}16}$ to be inspected in accordance with the inspection schedule.

Following capture by the camera unit 8, the pairs of images of the printing screen 2 and the workpiece W, as captured from each successive inspection site $IS_{2, 4\text{-}11, 14\text{-}16}$, are acquired (step 207) to allow for image processing.

In this embodiment the acquired screen and workpiece images are pixelated and defined by a pixel grid PG. Reference is again made to FIGS. 9 and 10 which illustrate corresponding parts (region R1 in FIG. 7) of the acquired screen and workpiece images, each having the same pixel grid PG.

Following acquisition of the pair of screen and workpiece images as captured from the second inspection site $IS_2$, an image processing routine (step 209) is then performed.

The image processing routine (step 209) will now be described hereinbelow with reference to FIG. 14.

A first pixel of the screen image is obtained from the image data (step 209(1)), and checked (step 209(2)) to classify the screen pixel as corresponding to the body of the printing screen 2, in this embodiment as characterized by a light pixel having an intensity above the set aperture threshold value, or an aperture, in this embodiment as characterized, by a dark pixel having an intensity below the set aperture threshold value.

As mentioned hereinabove, in an alternative embodiment, with a different lighting arrangement, the body of the printing screen 2 could be characterized by dark pixels and the apertures in the printing screen 2 characterized by light pixels. In this embodiment the checking step (step 209(2)) would classify the screen pixel as being of an aperture where the pixel has an intensity above the set aperture threshold value.

Where the screen pixel is classified as being of an aperture, namely, an aperture pixel, the screen pixel is assigned to an aperture (step 209(3)), a pixel count for that aperture is incremented (step 209(4)), and the corresponding pixel from the workpiece image, in this embodiment as mapped by utilizing the offset look-up table, is obtained (step 209(5)).

Reference is again made to FIG. 11, which illustrates the same screen image as that of FIG. 9, and identifies the pixels $P_1, P_2, P_3$ assigned to each of the respective apertures $A_1, A_2, A_3$, with the pixels $P_1$ of the first aperture $A_1$ being designated by a forward slash, the pixels $P_2$ of the second aperture $A_2$ being designated by a backward slash, and the pixels $P_3$ of the third aperture $A_3$ being designated by a cross.

The obtained workpiece pixel is then checked (step 209(6)) to determine if that workpiece pixel corresponds to deposit, in this embodiment as characterized by a dark pixel having an intensity below the set deposit threshold value.

As again mentioned hereinabove, in an alternative embodiment, with a different lighting arrangement, deposit could be characterized by light pixels. In this embodiment the checking step (step 209(6)) would classify a workpiece pixel as corresponding to deposit where having an intensity above the set deposit threshold value.

Where the workpiece pixel is classified as being of deposit, a deposit pixel count, which is a counterpart to the aperture pixel count, is incremented (step 209(7)).

Reference is again made to FIG. 12, which illustrates the same workpiece image as that of FIG. 10 and identifies the counterpart pixels, with the counterpart pixels $P_D$ classified as being of deposit $D_1, D_2, D_3$ being designated by a forward slash and the counterpart pixels $P_S$ classified as being of one of the structures $S_1, S_2, S_3$ being designated by a backward slash.

Subsequently, or where the screen pixel is not classified as being of an aperture in the screen pixel checking step (step 209(2)), a check (step 209(8)) is made as to whether the screen pixel is the last pixel in the screen image.

Where the screen pixel is not the last pixel in the screen image, the next screen pixel is obtained (step 209(1)) from the screen image, and the above-described pixel classification sub-routine (steps 209(2) to 209(7)) is repeated.

Where the screen pixel is the last pixel in the screen image, then, for each aperture, the percentage of deposit coverage is determined (step 209(9)) from the deposit pixel count as referenced to the aperture pixel count.

The determined percentages are then stored for the second inspection site $IS_2$ (step 209(10)).

Referring again to FIG. 13, a check (step 210) is then made as to whether the second inspection site $IS_2$ is the last to be inspected.

Where the second inspection site $IS_2$ is not the last to be inspected, the image acquisition step (step 207) and the image processing routine (step 209) are repeated for the next, in this embodiment fourth inspection site $IS_4$.

This process is then repeated for each of the further inspection sites $IS_{5\text{-}11, 14\text{-}16}$ to be image processed as defined by the inspection schedule.

Following completion of the image processing, the inspection results, as percentages of deposit coverage where determined by reference to respective apertures, are displayed (step 211).

Another embodiment of the inspection routine will now be described hereinbelow with reference to FIG. 15.

In this embodiment the inspection routine allows the operator to select enhanced image processing where the workpiece W being printed is of a kind which would merit such enhanced image processing. As will become apparent hereinbelow, this enhanced image processing finds particular application in relation to the inspection of workpieces W which include structures which are to be over-printed by deposit in the printing operation, that is, where deposit extends onto the body of the workpieces W, and the body of the workpieces W is imaged as one of dark or light regions similarly to the deposit.

In a first step, the operator is presented with the option of whether to employ enhanced image processing in respect of the workpiece W to be printed (step 301).

Where the operator selects enhanced image processing, an enhanced image processing flag is set to designate that the enhanced image processing routine is to be employed (step 302).

Where the operator does not select enhanced image processing, the enhanced image processing flag is not set such that the normal or standard image processing routine is employed.

Following the loading of a workpiece W, alignment and printing of the workpiece W, and separation of the workpiece W from the printing screen 2 to a vision height, and from the starting position as defined by the inspection schedule, in this embodiment the second inspection site $IS_2$, scanning of the camera unit 8 over the surface of the workpiece W, in this embodiment in line-by-line fashion by moving the camera unit 8 laterally and advancing the camera unit 8 forwardly at a lateral edge of the workpiece W, is commenced, such as successively to capture corresponding pairs of images of the printing screen 2 and the workpiece W at the plurality of inspection sites $IS_{2, 4-11, 14-16}$ in accordance with the inspection schedule (step 303). Reference is again made to FIG. 7 which represents this mode of scanning, where the camera unit 8 is scanned over the workpiece W along a scanning path SP and images of the printing screen 2 and the workpiece W are captured at the plurality of inspection sites $IS_{2, 4-11, 14-16}$ in accordance with the inspection schedule.

In this embodiment, where the camera unit 8 has strobed lighting for image capture on-the-fly, the speed of movement of the camera unit 8 is controlled to provide that the camera unit 8 is located at each successive inspection site $IS_{2, 4-11, 14-16}$, as defined by the inspection schedule, in correspondence with the frame rate of the camera unit 8, with the camera unit 8 being accelerated as necessary, for example, between the second and fourth inspection sites $IS_2$, $IS_4$ which are not adjacent.

When the camera unit 8 is located at the second inspection site $IS_2$, the camera unit 8 is triggered (step 304) such as to capture the corresponding pair of images of the printing screen 2 and the workpiece W at the second inspection site $IS_2$, which captured screen and workpiece images are acquired, in this embodiment by the control unit 11, and subsequently processed, as will be described in more detail hereinbelow.

A check (step 305) is then made as to whether the second inspection site $IS_2$ is the last to be inspected.

Where the second inspection site $IS_2$ is the last to be inspected, the camera unit 8 is then parked (step 306) and no further images are captured by the camera unit 8.

Where the second inspection site $IS_2$ is not the last to be inspected, the camera unit 8 is triggered (step 304) such as to capture the corresponding pair of images of the printing screen 2 and the workpiece W of the next, in this embodiment fourth inspection site $IS_4$, which captured screen and workpiece images are again acquired, in this embodiment by the control unit 11, and subsequently processed, as will be described in more detail hereinbelow.

This process is then repeated for each of the further inspection sites $IS_{5-11, 14-16}$ to be inspected in accordance with the inspection schedule.

Following capture by the camera unit 8, the pairs of images of the printing screen 2 and the workpiece W, as captured from each successive inspection site $IS_{2, 4-11, 14-16}$, are acquired (step 307) to allow for image processing.

In this embodiment the acquired screen and workpiece images are pixelated and defined by a pixel grid PG. Reference is made to FIGS. 16 and 17 which illustrate corresponding parts (region R2 in FIG. 7) of the acquired screen and workpiece images, each having the same pixel grid PG. For ease of illustration, the pixel grid PG is illustrated as having a very coarse resolution, whereas, in practice, the resolution of the pixel grid PG would be much finer, such as to minimize any error introduced by edge effects, as will be described in more detail hereinbelow.

FIG. 16 illustrates another part (region R2 in FIG. 7) of the acquired screen image, where encompassing two equi-sized, circular apertures $A_1$, $A_2$.

FIG. 17 illustrates the corresponding part (region R2 in FIG. 7) of the corresponding acquired workpiece image, where encompassing two equi-sized circular structures $S_1$, $S_2$ having deposits $D_1$, $D_2$ printed thereon.

A check (step 308) is then made of the enhanced image processing flag to determine whether enhanced image processing has been selected.

Where enhanced image processing has not been selected, a first, standard image processing routine (step 309a) is performed.

The standard image processing routine (step 309a) will now be described hereinbelow with reference to FIG. 18.

A first pixel of the screen image is obtained from the image data (step 309a(1)), and checked (step 309a(2)) to classify the screen pixel as corresponding to the body of the printing screen 2, in this embodiment as characterized by a light pixel having an intensity above the set aperture threshold value, or an aperture, in this embodiment as characterized by a dark pixel having an intensity below the set aperture threshold value.

As mentioned hereinabove, in an alternative embodiment, with a different lighting arrangement, the body of the printing screen 2 could be characterized by dark pixels and the apertures in the printing screen 2 characterized by light pixels. In this embodiment the checking step (step 309a(2)) would classify the screen pixel as being of an aperture where the pixel has an intensity above the set aperture threshold value.

Where the screen pixel is classified as being of an aperture, namely, an aperture pixel, the screen pixel is assigned to an aperture (step 309a(3)), a pixel count for that aperture is incremented (step 309a(4)), and the corresponding pixel from the workpiece image, in this embodiment as mapped by utilizing the offset look-up table, is obtained (step 309a(5)).

Reference is made to FIG. 19, which illustrates the same screen image as that of FIG. 16, and identifies the pixels $P_1$, $P_2$ assigned to each of the respective apertures $A_1$, $A_2$, with the pixels $P_1$ of the first aperture $A_1$ being designated by a forward slash, and the pixels $P_2$ of the second aperture $A_2$ being designated by a backward slash.

The obtained workpiece pixel is then checked (step 309a(6)) to determine if that workpiece pixel corresponds to deposit, in this embodiment as characterized by a dark pixel having an intensity below the set deposit threshold value.

As again mentioned hereinabove, in an alternative embodiment, with a different lighting arrangement, deposit could be characterized by light pixels. In this embodiment the checking step (step 309a(6)) would classify a workpiece pixel as corresponding to deposit where having an intensity above the set deposit threshold value.

As described hereinabove in relation to the inspection routine of the first-described embodiment, and exemplified in relation to the screen and workpiece images of FIGS. 11 and 12, such classification of deposit accurately characterizes deposits where the deposits do not extend beyond the extent of the underlying structures, as the image intensities of deposit and structure have a marked contrast, in being light and dark regions which can be readily distinguished.

However, such classification of deposit does not so accurately characterize deposits where the deposits are printed so as to extend beyond the extent of the underlying structures and the image intensities of the deposit and the body of the workpiece W are both one of below or greater than the set deposit threshold value, as, in such circumstances, deposit cannot be distinguished from the body of the workpiece W.

Reference is made to FIG. 20, which illustrates the same workpiece image as that of FIG. 17 and identifies the counterpart pixels to the aperture pixels of the screen image, with the counterpart pixels $P_D$ classified as being of deposit being designated by a forward slash and the counterpart pixels $P_O$ classified as being of other than deposit, in this embodiment one of the structures $S_1$, $S_2$, being designated by a backward slash.

As will be noted clearly from FIG. 20, where the apertures $A_1$, $A_2$ have a size greater than the counterpart structures $S_1$, $S_2$ on the workpiece W and the workpiece pixels corresponding both to deposit and the body of the workpiece W have an intensity below the set deposit threshold value, workpiece pixels corresponding to the body of the workpiece W are improperly classified as deposit. As mentioned hereinabove, with the alternative lighting arrangement, deposit and the body of the workpiece W would be characterized by light pixels, and thus both have an image intensity greater than the set deposit threshold value.

This improper classification of the pixels corresponding to the body of the workpiece W leads to improper characterization of the deposits $D_1$, $D_2$, as, although both of the illustrated deposits $D_1$, $D_2$ are clearly incomplete, classification of the pixels corresponding to the body of the workpiece W as deposit would result in the deposits $D_1$, $D_2$ being characterized as being near 100% complete.

Where the workpiece pixel is classified as being of deposit, a deposit pixel count, which is a counterpart to the aperture pixel count, is incremented (step $309a(7)$).

Subsequently, or where the screen pixel is not classified as being of an aperture in the screen pixel checking step (step $309a(2)$), a check (step $309a(8)$) is made as to whether the screen pixel is the last pixel in the screen image.

Where the screen pixel is not the last pixel in the screen image, the next screen pixel is obtained (step $309a(1)$) from the screen image, and the above-described pixel classification sub-routine (steps $309a(2)$ to $309a(7)$) is repeated.

Where the screen pixel is the last pixel in the screen image, then, for each aperture, the percentage of deposit coverage is determined (step $309a(9)$) from the deposit pixel count as referenced to the aperture pixel count.

The determined percentages are then stored for the second inspection site $IS_2$ (step $309a(10)$).

Referring again to FIG. 15, where enhanced image processing has been selected, a second, enhanced image processing routine (step $309b$) is performed.

The enhanced image processing routine (step $309b$) will now be described hereinbelow with reference to FIG. 21.

A first pixel of the screen image is obtained from the image data (step $309b(1)$), and checked (step $309b(2)$) to classify the screen pixel as corresponding to the body of the printing screen 2, in this embodiment as characterized by a light pixel having an intensity above the set aperture threshold value, or an aperture, in this embodiment as characterized by a dark pixel having an intensity below the set aperture threshold value.

As mentioned hereinabove, in an alternative embodiment, with a different lighting arrangement, the body of the printing screen 2 could be characterized by dark pixels and the apertures in the printing screen 2 characterized by light pixels. In this embodiment the checking step (step $309b(2)$) would classify the screen pixel as being of an aperture where the pixel has an intensity above the set aperture threshold value.

Where the screen pixel is classified as being of an aperture, namely, an aperture pixel, the screen pixel is assigned to an aperture (step $309b(3)$), and a pixel count for that aperture is incremented (step $309b(4)$).

Reference is again made to FIG. 19, which illustrates the same screen image as that of FIG. 16, and identifies the pixels $P_1$, $P_2$ assigned to each of the respective apertures $A_1$, $A_2$, with the pixels $P_1$ of the first aperture $A_1$ being designated by a forward slash, and the pixels $P_2$ of the second aperture $A_2$ being designated by a backward slash.

Subsequently, or where the screen pixel is not classified as being of an aperture in the screen pixel checking step (step $309b(2)$), a check (step $309b(5)$) is made as to whether the screen pixel is the last pixel in the screen image.

Where the screen pixel is not the last pixel in the screen image, the next screen pixel is obtained (step $309b(1)$) from the screen image, and the above-described pixel classification sub-routine (steps $309b(2)$ to $309b(4)$) is repeated.

Where the screen pixel is the last pixel in the screen image, then a first aperture is identified in the screen image (step $309b(6)$).

A check (step $309b(7)$) is then performed to determine whether the first aperture is to be subjected to enhanced image processing.

In this embodiment the apertures which are to be subjected to enhanced image processing are identified by at least one predetermined geometrical characteristic thereof, here both shape and size, such that all of the apertures which have the at least one geometrical characteristic are subjected to enhanced image processing, with the at least one geometrical characteristic being representative of apertures through which deposit is to be over-printed onto corresponding structures on a workpiece W.

In an alternative embodiment all of the apertures could be subjected to enhanced image processing.

Where the first aperture is to be subjected to enhanced image processing, a set of pixels, which have a predetermined relationship to the set of aperture pixels which define the first aperture, are determined as inspection pixels (step $309b(8)$). In this embodiment each set of inspection pixels is centrally located within the region defined by the respective set of aperture pixels and defines a region which is of such a smaller size than the region defined by the set of aperture pixels that, within reasonable limits of confidence, the workpiece pixels corresponding to the inspection pixels can only overly a structure on the workpiece W, and thus only correspond either to the structure or deposit printed thereon. In a preferred embodiment the region defined by a set of inspection pixels has a lateral dimension which is about one-third that defined by the respective set of aperture pixels.

Following determination of the set of inspection pixels for the first aperture, the corresponding pixels in the workpiece image, in this embodiment as mapped by utilizing the offset look-up table, are obtained (step $309b(9)$), and the intensity values for each of those workpiece pixels is determined (step $309b(10)$). Where any of the corresponding workpiece pixels is of structure, in this embodiment as characterized by a light pixel having an intensity greater than that of the set deposit threshold value by a predetermined amount, those workpiece pixels are disregarded. As again mentioned hereinabove, in an alternative embodiment, with a different lighting arrangement, structure could be characterized by dark pixels. In this embodiment any corresponding workpiece pixels would be disregarded where having an intensity below that of the set deposit threshold value by a predetermined amount.

Reference is made to FIGS. 22 and 23 which correspond to FIGS. 19 and 20 and show both the sets of inspection pixels $P_I$ within the respective sets of aperture pixels $P_1$, $P_2$ which define the first and second apertures $A_1$, $A_2$ and the corresponding workpiece pixels $P_W$, with the inspection pixels $P_I$ and the workpiece pixels $P_W$ being both designated by a cross.

From the determined intensity values of the corresponding workpiece pixels, maximum and minimum intensity values are obtained, and in this embodiment a specific deposit threshold value is set for the aperture by assigning these values as upper and lower bounding limits for the deposit threshold value for the aperture (step 309b(11)). As mentioned hereinabove, by setting upper and lower bounds to the deposit threshold value, deposit can be more precisely distinguished from the body of the workpiece W in subsequent image processing, where the body of the workpiece W can often be difficult to distinguish from deposit.

Subsequently, or where the first aperture is determined in the enhanced image processing checking step (step 309b(7)) as not to be subjected to enhanced image processing, a check (step 309b(12)) is then made as to whether the aperture is the last in the screen image.

Where the aperture is not the last in the screen image, the above-described deposit threshold value setting sub-routine (steps 309b(6) to 309b(11)) is repeated for the next aperture in the screen image.

This process is then repeated for each of the further apertures in the screen image.

Following setting of a specific deposit threshold value for each of the apertures to be subjected to enhanced image processing, a first workpiece pixel corresponding to a first of the already-assigned aperture pixels is obtained, in this embodiment as mapped by utilizing the offset look-up table, from the image data (step 309b(13)), and checked (step 309b(14)) to determine if that workpiece pixel corresponds to deposit. In this embodiment deposit is characterized by a dark pixel which, where the aperture is not subjected to enhanced image processing, has an intensity below the single, set deposit threshold value, and, where the aperture is subjected to enhanced image processing, has an intensity within the upper and lower bounding limits of the deposit threshold value as assigned to the aperture containing the aperture pixel.

As again mentioned hereinabove, in an alternative embodiment, with a different lighting arrangement, deposit could be characterized by light pixels. In this embodiment the checking step (step 309b(14)) would, where the aperture is not subjected to enhanced image processing, classify a workpiece pixel as corresponding to deposit where having an intensity above the single, set deposit threshold value, and, where the aperture is subjected to enhanced image processing, classify a workpiece pixel as corresponding to deposit where having an intensity within the upper and lower bounding limits of the deposit threshold value as assigned to the aperture containing the aperture pixel.

Reference is made to FIG. 24, which illustrates the same workpiece image as that of FIG. 17 and identifies the counterpart pixels to the aperture pixels of the apertures $A_1$, $A_2$ in the screen image, with the counterpart pixels $P_D$ classified as being of deposit being designated by a forward slash and the counterpart pixels $P_O$ classified as being of other than deposit being designated by a backward slash. As will be evident, particularly through comparison with the workpiece image of FIG. 20, the workpiece pixels have been subjected to enhanced image processing, enabling the workpiece pixels corresponding to the deposits $D_1$, $D_2$ to be distinguished from those both of the structures $S_1$, $S_2$ and the body of the workpiece W, and thus providing for an accurate characterization of the deposits $D_1$, $D_2$.

Where the workpiece pixel is classified as being of deposit, a deposit pixel count, which is a counterpart to the aperture pixel count, is incremented (step 309b(15)).

A check (step 309b(16)) is then made as to whether the aperture pixel is the last of the assigned aperture pixels.

Where the aperture pixel is not the last of the assigned aperture pixels, the above-described pixel classification sub-routine (steps 309b(13) to 309b(15)) is repeated for the next aperture pixel.

Where the aperture pixel is the last aperture pixel, then, for each aperture, the percentage of deposit coverage is determined (step 309b(17)) from the deposit pixel count as referenced to the aperture pixel count.

The determined percentages are then stored for the second inspection site $IS_2$ (step 309b(18)).

Referring again to FIG. 15, a check (step 310) is then made as to whether the second inspection site $IS_2$ is the last to be inspected.

Where the second inspection site $IS_2$ is not the last to be inspected, the image acquisition step (step 307) and the image processing routine (step 309a/309b) are repeated for the next, in this embodiment fourth inspection site $IS_4$.

This process is then repeated for each of the further inspection sites $IS_{5-11,\ 14-16}$ to be image processed as defined by the inspection schedule.

Following completion of the image processing, the inspection results, as percentages of deposit coverage where determined by reference to respective apertures, are displayed (step 311).

The inspection results can be presented in many different ways, depending upon the requirements of the operator. In one embodiment the deposit coverage can be presented to the operator as one of a PASS, WARNING or FAIL indicator, where PASS is indicative of the percentage exceeding an optimal level, WARNING is indicative of the percentage exceeding an acceptable, but not optimal, level, and FAIL is indicative of the percentage being below a required level. The presentation can take any form, for example, tabular, graphical or pictorial format, and could include worst case percentages.

In one embodiment the image processing can be configured such as to ignore any incomplete apertures which extend to an edge of the acquired screen images. Such incomplete imaged apertures could give rise to false results, particularly where percentages of deposit coverage are determined for each deposit.

In one alternative embodiment the set-up routine can provide for the positioning and sizing of the inspection sites $IS_{1-16}$ such that the borders of the inspection sites $IS_{1-16}$ do not intersect apertures in the printing screen 2.

In another alternative embodiment, instead of precisely positioning and sizing the inspection sites $IS_{1-16}$ as in the afore-mentioned alternative embodiment, the inspection sites $IS_{1-16}$ could be configured such as to overlap. Although such overlapping would result in duplication of image processing for the edge regions of the inspection sites $IS_{1-16}$, in relative terms the amount of additional image processing would be relatively small.

As will be appreciated, the inspection system of the present invention enables the utilization of far simpler image processing, thereby significantly decreasing inspection times and providing for the inspection of a greater number of inspection sites, and does not require pre-programming of the features to be inspected at each inspection site, typically apertures in the printing screen 2 and structures on a workpiece W.

The image processing first involves the processing of the image of the printing screen 2, which screen image is a simple image, in this embodiment of small dark regions, which correspond to apertures, surrounded by a bright region, which corresponds to the body of the printing screen 2. Such image processing, in utilizing the intensity of pixels of the screen image, merely requires the simple characterization of distinct dark and light regions, which characterization can be achieved using an aperture threshold value. Only following the classification of a screen pixel as corresponding to an aperture does the image processing extend to the processing of the image of the workpiece W, and then only the corresponding pixel of the workpiece image. This image processing is significantly simpler in requiring the processing of only ones of the pixels of the workpiece image, as compared to the image processing employed in current screen printing machines which requires the entire workpiece image to be processed. Also, in only processing workpiece pixels which correspond in position to an aperture in the printing screen 2, the workpiece pixels should only be either dark pixels, in this embodiment of deposit, or light pixels, in this embodiment, of an unprinted structure, thereby only requiring the simple characterization of distinct dark and light regions, which characterization can be achieved using a deposit threshold value, as either a single value or a value having upper and lower bounds. In the image processing employed in current screen printing machines, which requires the entire workpiece image to be processed, the processing required is far more complex as many different features, each having a different intensity have to be distinguished from one another.

Furthermore, in not utilizing pre-programmed features, typically apertures in the printing screen 2 and structures on a workpiece W, as a means of reference to characterize printed deposits, but instead mapping simultaneously-captured screen and workpiece images, the camera unit 8, which is used to capture the screen and workpiece images, does not need to be precisely positioned. Indeed, by not requiring the precise positioning of the camera unit 8, which would typically require the camera unit 8 to be stationary or at least slowed considerably, a moving camera unit 8 can be employed, allowing the images to be captured on-the-fly. In this embodiment, which utilizes a set-up routine to determine any offset in the captured pairs of screen and workpiece images at each inspection site, the position of the camera unit 8 is referenced, but this referencing is only utilized to designate the inspection site, and then the referencing, by way of correcting the workpiece image for any image offset relative to the corresponding screen image, is performed subsequent to the image capture.

Finally, it will be understood that the present invention has been described in its preferred embodiments and can be modified in many different ways without departing from the scope of the invention as defined by the appended claims.

In this embodiment the camera unit 8 utilizes area-view cameras to capture area-view images of the printing screen 2 and the workpiece W at each inspection site. In an alternative embodiment, line-scan cameras could be utilized which scan continuously across the printing screen 2 and the workpiece W.

In alternative embodiments, instead of building a table for each imaged aperture, and hence deposit, a table could be built either for each inspection site by recording an aperture count and a deposit count for the pixels assigned to each entire inspection site, or for each workpiece W by recording an aperture count and a deposit count for the pixels assigned to all of the inspection sites.

In this embodiment the camera unit 8 captures images of the imaged inspection sites on-the-fly through the use of strobed lighting. In an alternative embodiment, however, the inspection system could be configured such as to provide for the camera unit 8 to be stationary when capturing images, thereby avoiding the need for strobed lighting.

In another alternative embodiment, based on the knowledge that there can be a small, but significant, intensity value difference between aperture pixels corresponding to clear aperture and blocked aperture, where a low percentage deposit coverage is detected for an aperture, the aperture pixels for the aperture could be checked using a similar principle to the enhanced image processing routine as described hereinabove in relation to FIG. 21 to discriminate between clear aperture pixels and blocked aperture pixels, and thus provide for characterization of aperture blockage for the aperture. In this embodiment the presence of deposit on the workpiece W can, with a high level of confidence, be assigned as corresponding to clear aperture. Thus, by identifying a set of workpiece pixels which correspond to deposit, typically corresponding to a central region of the counterpart aperture, the counterpart set of aperture pixels can be assigned as corresponding to clear aperture. For this set of aperture pixels, upper and lower image intensity values are determined, and upper and lower bounding limits set for the aperture threshold value. Then, subsequently, all of the aperture pixels for the aperture can be processed to classify the aperture pixels as corresponding either to clear aperture, where the image intensity value falls within the bounding limits set for the aperture threshold value, or blocked aperture, where the image intensity value falls outside the bounding limits set for the aperture threshold value. With the aperture pixels so classified, a percentage blocked value can then be determined for the aperture.

In this embodiment, in the inspection routine, the image processing of corresponding pairs of screen and workpiece images from the inspection sites is performed subsequent to the acquisition of those pairs of images. In one alternative embodiment, the signals derived from the corresponding captured images of the printing screen 2 and the workpiece W, where synchronized such that the signals from the cameras are of corresponding pixels from the screen and workpiece images, can be compared directly, where the cameras of the camera unit 8 could be full-view cameras or line-scan cameras.

In another alternative embodiment the image processing of corresponding pairs of screen and workpiece images from the inspection sites can be commenced whilst image acquisition is on-going, provided that the pixels assigned to corresponding parts of the screen and workpiece images have been acquired.

In this embodiment the image acquisition and image processing is performed by the control unit 11 of the screen printing machine. In an alternative embodiment the camera unit 8 could be configured to perform at least the image acquisition, and in one embodiment also the image processing.

In this embodiment the cameras of the camera unit 8 utilize integration to capture the screen and workpiece images. In an alternative embodiment, the cameras of the camera unit 8 could be shuttered cameras which capture the screen and workpiece images through by shuttering the printing screen 2 and the workpiece W.

FIG. 25 schematically illustrates a representation of an inspection circuit for providing for the direct comparison of the output signals of the screen and workpiece cameras of the camera unit 8 in characterizing deposits printed on a workpiece W. In this embodiment the cameras of the camera unit 8 are area-view cameras, but in another embodiment could be line-scan cameras.

The inspection circuit includes an examine/ignore signal generator 15 which receives the output signal of the screen camera, and outputs an examine/ignore signal which has a first, ignore state IGNORE where the output signal of the screen camera has an intensity above a set aperture threshold value, which is representative of the output signal corresponding to the body of the printing screen 2, or a second, examine state EXAMINE where the output signal of the screen camera has an intensity below the set aperture threshold value, which is representative of the output signal corresponding to an aperture in the printing screen 2. As in the above-described embodiment, the aperture threshold value can be trained.

The output signal of the screen camera, in this embodiment an analogue signal, has an intensity which varies in accordance with the intensity of the respective imaged point in the screen image. Referring to FIG. 26, the output signal of the screen camera comprises in series the output for each respective image line n, n+1, n+2, with the output of each image line being separated by a synchronisation period SYNC, during which the image is blanked. In this embodiment each image line comprises first, high regions which correspond to the body of the printing screen 2 and second, low regions which correspond to apertures in the printing screen 2.

The examine/ignore signal generator 15 further receives an enable signal which acts to control the examine/ignore signal generator 15 such that the examine/ignore signal has the ignore state IGNORE where the enable signal is not present. Through the use of the enable signal, the inspection can be limited to images that actually require inspection. Typically, a blank image could appear as one large aperture.

The inspection circuit further includes a deposit absent/present signal generator 17 which receives the output signal of the examine/ignore signal generator 15 and the output signal of the workpiece camera.

The output signal of the workpiece camera, in this embodiment an analogue signal, has an intensity which varies in accordance with the intensity of the respective imaged point in the workpiece image. Referring to FIG. 26, the output signal of the workpiece camera has the same format as the output signal of the screen camera, that is, comprising in series the output for each respective workpiece image line n, n+1, n+2 corresponding to the respective screen image line, with the output of each workpiece image line being separated by a synchronisation period SYNC, during which the image is blanked. Each workpiece image line comprises regions of widely-varying intensity. Ordinarily, such regions of widely-varying intensity would render image processing difficult, but, significantly, in this embodiment each workpiece image line includes distinct regions of low intensity which correspond to deposits printed on the workpiece W.

While the examine/ignore signal of the examine/ignore signal generator 15 has the ignore state IGNORE, the deposit absent/present signal generator 17 outputs an absent/present signal which has a first, absent state ABSENT.

Where the output signal of the examine/ignore signal generator 15 has the examine state EXAMINE, the deposit absent/present signal generator 17 outputs an absent/present signal which has the first, absent state ABSENT where the output signal of the workpiece camera has in this embodiment an intensity above a set deposit threshold value, which is representative of the workpiece signal corresponding to other than deposit, or a second, present state PRESENT where the output signal of the workpiece camera has in this embodiment an intensity below the set deposit threshold value, which is representative of the workpiece signal corresponding to deposit. As in the above-described embodiment, the deposit threshold value can be trained.

The inspection circuit further includes a print characteristic determiner 19 for determining a print characteristic from the output signals of the examine/ignore signal generator 15 and the deposit absent/present signal generator 17. The print characteristic determiner 19 is operative to determine a print characteristic, typically a representation of percentage of deposit coverage, for example, as a PASS, WARNING or FAIL representation, where PASS is indicative of the percentage exceeding an optimal level, WARNING is indicative of the percentage exceeding an acceptable, but not optimal, level, and FAIL is indicative of the percentage being below a required level, by referencing the relative durations of the output signal of the deposit absent/present signal generator 17 having a present state PRESENT as compared to the output signal of the examine/ignore signal generator 15 having an examine state EXAMINE. By selection of each inspection site to include only one aperture, and hence print deposit, the percentage of deposit coverage can be determined for each deposit. Alternatively, the inspection sites can include a plurality of apertures, and hence print deposits, and the resulting percentage of deposit coverage represents an average value for the deposits in the inspection site. As with the above-described first embodiment, the representation of the percentages of deposit coverage can take many different forms.

In one alternative embodiment, with a different lighting arrangement, the output signal of the screen camera could have an intensity below the set aperture threshold value where corresponding to the body of the printing screen 2 and an intensity above the set aperture threshold value where corresponding to an aperture in the printing screen 2. In this embodiment the examine/ignore signal generator 15 would be configured to output an examine/ignore signal which has a first, ignore state IGNORE where the output signal of the screen camera has an intensity below the set aperture threshold value and a second, examine state EXAMINE where the output signal of the screen camera has an intensity above the set aperture threshold value.

In another alternative embodiment, with a different lighting arrangement, the output signal of the workpiece camera could have an intensity below the set deposit threshold value where corresponding to other than deposit and an intensity above the set deposit threshold value where corresponding to deposit. In this embodiment the deposit absent/present signal generator 17 would be configured to output an absent/present signal which has an absent state ABSENT where the output signal of the workpiece camera has an intensity below the set deposit threshold value, and a present state PRESENT where the output signal of the workpiece camera has an intensity above the set deposit threshold value.

The invention claimed is:

1. An inspection system for inspecting deposits printed on workpieces through a printing screen, the system comprising:
    a camera unit movable relative to a printing screen, where comprising a body including a plurality of apertures, and a workpiece on which deposits are printed through the apertures of the printing screen;
    wherein the camera unit captures images of at least one pair of corresponding regions of a lower surface of the printing screen and an upper surface of the workpiece; and
    a processor configured to process the images to determine, in turn, for each of a plurality of points defining the image of the printing screen, the image of the printing screen comprising both the body of the printing screen and apertures within the printing screen, whether the point is of aperture, and, only where the point is determined to be of aperture, determine whether the corresponding point of the corresponding image of the workpiece, as defined by a corresponding plurality of points, is of deposit, thereby enabling a determination of a print characteristic of deposits printed on the workpiece from a relationship of the points determined to be of deposit to the points determined to be of aperture.

2. The system of claim 1, wherein the camera unit is operable simultaneously to capture images of the printing screen and the workpiece.

3. The system of claim 1, wherein the camera unit is a full-area camera unit for capturing full-area images of the printing screen and the workpiece.

4. The system of claim 1, wherein the camera unit is a line-scan camera unit for capturing line-scan images of the printing screen and the workpiece.

5. The system of claim 1, wherein the processor is configured simultaneously to process the images of the printing screen and the workpiece during image capture by the camera unit.

6. The system of claim 1, wherein the processor is configured to process the captured images subsequent to acquisition.

7. The system of claim 1, wherein the images of the printing screen and the workpiece are defined by respective ones of screen and workpiece signals having intensities in dependence upon the imaged features, with the points defining each of the images being time-sliced components of the respective screen and workpiece signals.

8. The system of claim 7, wherein the relationship of the points determined to be of deposit to the points determined to be of aperture is determined from a time count of a time for which the workpiece signal is determined to be of deposit relative to a time for which the screen signal is determined to be of aperture.

9. The system of claim 1, wherein the images of the printing screen and the workpiece are pixelated images, with the points defining each of the images being pixels of the pixelated images.

10. The system of claim 9, wherein the relationship of the points determined to be of deposit to the points determined to be of aperture is determined from a number count of the number of pixels determined to be of deposit relative to the number of pixels determined to be of aperture.

11. The system of claim 9, wherein the processor is configured to acquire a plurality of pairs of corresponding images of the printing screen and the workpiece in accordance with an inspection schedule defining a plurality of inspection sites at which images are in use acquired.

12. The system of claim 11, wherein the inspection sites of the inspection schedule are determined in a set-up routine.

13. The system of claim 12, wherein an offset in the corresponding pair of images of the printing screen and the workpiece as acquired by the camera unit at each inspection site is predetermined, such that the pixel in an image of the workpiece corresponding to a pixel in the corresponding image of the printing screen is determined in accordance with the offset.

14. The system of claim 11, wherein the print characteristic comprises a representation of a percentage of a determined deposit coverage as compared to an expected deposit coverage, and the print characteristic is provided as a plurality of representations for the inspection sites.

15. The system of claim 14, wherein the representation for each inspection site is of a worst case deposit in the respective inspection site.

16. The system of claim 14, wherein the representation for each inspection site comprises a plurality of representations corresponding to at least ones or groups of ones of the deposits in the respective inspection site.

17. The system of claim 1, wherein the print characteristic comprises a representation of a percentage of a determined deposit coverage as compared to an expected deposit coverage.

18. The system of claim 17, wherein the print characteristic is provided as a representation for all deposits.

19. The system of claim 18, wherein the representation is of a worst case deposit.

20. The system of claim 1, wherein the points determined to be of deposit are determined by reference to a reference threshold value of image intensity.

21. The system of claim 20, wherein, for at least one of the apertures, the points determined to be of deposit are determined as having an image intensity one of above or below a reference threshold value of image intensity.

22. The system of claim 20, wherein, for at least one of the apertures, the points determined to be of deposit are determined as having an image intensity within upper and lower bounding limits of a reference threshold value of image intensity.

23. A screen printing machine incorporating the inspection system of claim 1.

24. A method of inspecting deposits printed on workpieces through a printing screen, the method comprising the steps of:

capturing images of at least one pair of corresponding regions of a lower surface of a printing screen, where comprising a body including a plurality of apertures, and an upper surface of a workpiece on which deposits are printed through the apertures of the printing screen; and processing the images to determine, in turn, for each of a plurality of points defining the image of the printing screen, the image of the printing screen comprising both the body of the printing screen and apertures within the printing screen, whether the point is of aperture, and, only where the point is determined to be of aperture, determine whether the corresponding point of the corresponding image of the workpiece, as defined by a corresponding plurality of points, is of deposit, thereby enabling a determination of a print characteristic of deposits printed on the workpiece from a relationship of the points determined to be of deposit to the points determined to be of aperture.

25. The method of claim 24, wherein the images of the printing screen and the workpiece are captured simultaneously.

26. The method of claim 24, wherein full-area images are captured of the printing screen and the workpiece.

27. The method of claim 24, wherein line-scan images are captured of the printing screen and the workpiece.

28. The method of claim 24, wherein the image capture and processing steps are performed simultaneously.

29. The method of claim 24, wherein the processing step is performed subsequent to the image capture step.

30. The method of claim 24, wherein the images of the printing screen and the workpiece are defined by respective ones of screen and workpiece signals having intensities in dependence upon the imaged features, with the points defining each of the images being time-sliced components of the respective screen and workpiece signals.

31. The method of claim 30, wherein the relationship of the points determined to be of deposit to the points determined to be of aperture is determined from a time count of a time for which the workpiece signal is determined to be of deposit relative to a time for which the screen signal is determined to be of aperture.

32. The method of claim 24, wherein the images of the printing screen and the workpiece are pixelated images, with the points defining each of the images being pixels of the pixelated images.

33. The method of claim 32, wherein the relationship of the points determined to be of deposit to the points determined to be of aperture is determined from a number count of the number of pixels determined to be of deposit relative to the number of pixels determined to be of aperture.

34. The method of claim 32, wherein, in the image capture step, a plurality of pairs of corresponding images of the printing screen and the workpiece are acquired at a plurality of inspection sites in accordance with an inspection schedule.

35. The method of claim 34, further comprising the step of:
performing a set-up routine to determine an inspection schedule defining a plurality of inspection sites at which images are to be acquired.

36. The method of claim 35, wherein, in the set-up routine, an offset in the corresponding pair of images of the printing screen and the workpiece at each inspection site is determined, and, in determining the pixel in an image of the workpiece corresponding to a pixel in the corresponding image of the printing screen, the pixel in the image of the workpiece corresponding to the pixel in the corresponding image of the printing screen is determined in accordance with the offset.

37. The method of claim 34, wherein the print characteristic comprises a representation of a percentage of a determined deposit coverage as compared to an expected deposit coverage, and the print characteristic is provided as a plurality of representations for the inspection sites.

38. The method of claim 37, wherein the representation for each inspection site is of a worst case deposit in the respective inspection site.

39. The method of claim 37, wherein the representation for each inspection site comprises a plurality of representations corresponding to at least ones or groups of ones of the deposits in the respective inspection site.

40. The method of claim 24, wherein the print characteristic comprises a representation of a percentage of a determined deposit coverage as compared to an expected deposit coverage.

41. The method of claim 40, wherein the print characteristic is provided as a representation for all deposits.

42. The method of claim 41, wherein the representation is of a worst case deposit.

43. The method of claim 24, wherein each corresponding point of the corresponding image of the workpiece is determined to be of deposit by reference to a reference threshold value of image intensity.

44. The method of claim 43, wherein, for at least one of the apertures, each corresponding point of the corresponding image of the workpiece is determined to be of deposit in having an image intensity one of above or below a reference threshold value of image intensity.

45. The method of claim 43, wherein, for at least one of the apertures, each corresponding point of the corresponding image of the workpiece is determined to be of deposit in having an image intensity within upper and lower bounding limits of a reference threshold value of image intensity.

* * * * *